US006977165B2

(12) United States Patent
Farmer

(10) Patent No.: US 6,977,165 B2
(45) Date of Patent: Dec. 20, 2005

(54) SEQUENCE SPECIFIC RECOMBINASE-BASED METHODS FOR PRODUCING INTRON CONTAINING VECTORS AND COMPOSITIONS FOR USE IN PRACTICING THE SAME

(75) Inventor: Andrew Alan Farmer, Mountain View, CA (US)

(73) Assignee: Clontech Laboratories, Inc., Mountain View, CA (US)

( * ) Notice: Subject to any disclaimer, the term of this patent is extended or adjusted under 35 U.S.C. 154(b) by 0 days.

(21) Appl. No.: 10/055,794

(22) Filed: Jan. 17, 2002

(65) Prior Publication Data

US 2003/0059900 A1 Mar. 27, 2003

Related U.S. Application Data

(60) Provisional application No. 60/263,358, filed on Jan. 18, 2001.

(51) Int. Cl.[7] ........................ C12N 15/00; C12N 15/64; C12N 15/74; C07H 21/02; C07H 21/04

(52) U.S. Cl. ................ 435/91.41; 435/91.4; 435/91.42; 435/471; 435/320.1; 536/23.1; 536/24.1; 536/24.2

(58) Field of Search ............................ 435/91.4, 320.1, 435/471, 69.1, 172.1, 172.3, 240.4, 91.41, 91.42; 536/23.1, 24.1, 24.2; 800/205; 935/30, 18, 35, 69, 67

(56) References Cited

U.S. PATENT DOCUMENTS

| | | | | |
|---|---|---|---|---|
| 5,527,695 | A | | 6/1996 | Hodges et al. |
| 5,744,336 | A | | 4/1998 | Hodges et al. |
| 5,851,808 | A | | 12/1998 | Elledge et al. |
| 5,888,732 | A | | 3/1999 | Hartley et al. |
| 5,962,255 | A | | 10/1999 | Griffiths et al. |
| 6,010,884 | A | * | 1/2000 | Griffiths et al. ............ 435/69.7 |

FOREIGN PATENT DOCUMENTS

| | | |
|---|---|---|
| WO | WO00/12687 | 3/2000 |
| WO | WO 00/60091 | 10/2000 |
| WO | WO01/05961 A1 | 1/2001 |

OTHER PUBLICATIONS

Kaartinen et al. "Removal of the floxed neo gene from a conditional knockout allele by the adenoviral Cre recombinase in vivo" *enesis* (2001) Nov. 31 (3):126–9.

Yoshimura et al. "Application of Cre–IoxP system to the urinary tract and cancer gene therapy" *Mol. Urol* (2001) Summer, 592):81–4.

Liu et al. "A mammalian gene expression vector with blue–white selection for efficient subcloning in Escherichia coli" *Anal. Biochemistry*(1997) 246:264–267.

Qinghua, et al. "The univector plasmid–fusion system, a method for rapid construction of recombinant DNA without restriction enzymes" *Current Biology, Current Science*, (1998) vol. 8(24): 1300–1309.

* cited by examiner

*Primary Examiner*—Gerry Leffers
*Assistant Examiner*—Maria Marvich
(74) *Attorney, Agent, or Firm*—Bret E. Field; Bozicevic, Field & Francis LLP

(57) ABSTRACT

Methods are provided for producing a vector that includes at least one splicable intron. In the subject methods, intron containing vectors are produced from donor and acceptor vectors that each include a site specific recombinase site, where the subject donor and acceptor vectors further include splice donor and acceptor sites that, upon site specific recombination of the donor and acceptor vectors, define an intron in the product vector of the recombination step. Also provided are compositions for use in practicing the subject methods, including the donor and acceptor vectors themselves, as well as systems and kits that include the same. The subject invention finds use in a variety of different applications, including the production of expression vectors that encode C-terminal tagged fusion proteins, the production of expression vectors that encode pure protein and not a fusion thereof, and the like.

19 Claims, 5 Drawing Sheets

```
                        SEQUENCE LISTING

<160> NUMBER OF SEQ ID NOS: 17

<210> SEQ ID NO 1
<211> LENGTH: 4938
<212> TYPE: DNA
<213> ORGANISM: Artificial Sequence
<220> FEATURE:
```

-continued

<223> OTHER INFORMATION: Synthetic Vector

<400> SEQUENCE: 1

```
gcggccgcat aacttcgtat agcatacatt atacgaagtt atcagtcgac ggtaccggac     60
atatgcccgg gaattcctgc aggatccgct cgagaagctt tctagaccat tcgtttggcg    120
cgcgggccca ggtgagtggt cataatcata atcataatca taatcataat cacaactagc    180
ctaggagatc ctggtcatga ctagtgcttg gattctcacc aataaaaaac gcccggcggc    240
aaccgagcgt tctgaacaaa tccagatgga gttctgaggt cattactgga tctatcaaca    300
ggagtccaag cgagctcgat atcaaattac gccccgccct gccactcatc gcagtactgt    360
tgtaattcat taagcattct gccgacatgg aagccatcac aaacggcatg atgaacctga    420
atcgccagcg gcatcagcac cttgtcgcct tgcgtataat atttgcccat ggtgaaaacg    480
ggggcgaaga agttgtccat attggccacg tttaaatcaa aactggtgaa actcacccag    540
ggattggctg agacgaaaaa catattctca ataaaccctt tagggaaata ggccaggttt    600
tcaccgtaac acgccacatc ttgcgaatat atgtgtagaa actgccggaa atcgtcgtgg    660
tattcactcc agagcgatga aaacgtttca gtttgctcat ggaaaacggt gtaacaaggg    720
tgaacactat cccatatcac cagctcaccg tctttcattg ccatacgaaa ttccggatga    780
gcattcatca ggcgggcaag aatgtgaata aaggccggat aaaacttgtg cttatttttc    840
tttacggtct ttaaaaaggc cgtaatatcc agctgaacgg tctggttata ggtacattga    900
gcaactgact gaaatgcctc aaaatgttct ttacgatgcc attgggatat atcaacggtg    960
gtatatccag tgattttttt ctccatttta gcttccttag ctcctgaaag atccataact   1020
tcgtatagca tacattatac gaagttatgc ggccgcgacg tccacatata cctgccgttc   1080
actattattt agtgaaatga gatattatga tattttctga attgtgatta aaaaggcaac   1140
tttatgccca tgcaacagaa actataaaaa atacagagaa tgaaaagaaa cagatagatt   1200
ttttagttct ttaggcccgt agtctgcaaa tccttttatg attttctatc aaacaaaaga   1260
ggaaaataga ccagttgcaa tccaaacgag agtctaatag aatgaggtcg aaaagtaaat   1320
cgcgcgggtt tgttactgat aaagcaggca agacctaaaa tgtgtaaagg gcaaagtgta   1380
tactttggcg tcacccctta catattttag gtcttttttt attgtgcgta actaacttgc   1440
catcttcaaa caggagggct ggaagaagca gaccgctaac acagtacata aaaaaggaga   1500
catgaacgat gaacatcaaa aagtttgcaa aacaagcaac agtattaacc tttactaccg   1560
cactgctggc aggaggcgca actcaagcgt ttgcgaaaga aacgaaccaa aagccatata   1620
aggaaacata cggcatttcc catattacac gccatgatat gctgcaaatc cctgaacagc   1680
aaaaaaatga aaaatatcaa gttcctgagt tcgattcgtc cacaattaaa aatatctctt   1740
ctgcaaaagg cctggacgtt tgggacagct ggccattaca aaacgctgac ggcactgtcg   1800
caaactatca cggctaccac atcgtctttg cattagccgg agatcctaaa aatgcggatg   1860
acacatcgat ttacatgttc tatcaaaaag tcggcgaaac ttctattgac agctggaaaa   1920
acgctggccg cgtctttaaa gacagcgaca aattcgatgc aaatgattct atcctaaaag   1980
accaaacaca agaatggtca ggttcagcca catttacatc tgacggaaaa atccgtttat   2040
tctacactga tttctccggt aaacattacg gcaaacaaac actgacaact gcacaagtta   2100
acgtatcagc atcagacagc tctttgaaca tcaacggtgt agaggattat aaatcaatct   2160
ttgacggtga cggaaaaacg tatcaaaatg tacagcagtt catcgatgaa ggcaactaca   2220
gctcaggcga caaccatacg ctgagagatc ctcactacgt agaagataaa ggccacaaat   2280
```

-continued

```
actttagtatt tgaagcaaac actggaactg aagatggcta ccaaggcgaa gaatctttat   2340
ttaacaaagc atactatggc aaaagcacat cattcttccg tcaagaaagt caaaaacttc   2400
tgcaaagcga taaaaaacgc acggctgagt tagcaaacgg cgctctcggt atgattgagc   2460
taaacgatga ttacacactg aaaaaagtga tgaaaccgct gattgcatct aacacagtaa   2520
cagatgaaat tgaacgcgcg aacgtcttta aaatgaacgg caaatggtac ctgttcactg   2580
actcccgcgg atcaaaaatg acgattgacg gcattacgtc taacgatatt tacatgcttg   2640
gttatgtttc taattcttta actggcccat acaagccgct gaacaaaact ggccttgtgt   2700
taaaaatgga tcttgatcct aacgatgtaa cctttactta ctcacacttc gctgtacctc   2760
aagcgaaagg aaacaatgtc gtgattacaa gctatatgac aaacagagga ttctacgcag   2820
acaaacaatc aacgtttgcg cctagcttcc tgctgaacat caaaggcaag aaaacatctg   2880
ttgtcaaaga cagcatcctt gaacaaggac aattaacagt taacaaataa aaacgcaaaa   2940
gaaaatgccg atatcctatt ggcattgacg tcaggtggca cttttcgggg aaatgtgcgc   3000
ggaaccccta tttgtttatt tttctaaata cattcaaata tgtatccgct catgagacaa   3060
taaccctgat aaatgcttca ataatattga aaaaggaaga gtatgagtat tcaacatttc   3120
cgtgtcgccc ttattccctt ttttgcggca ttttgccttc ctgtttttgc tcacccagaa   3180
acgctggtga aagtaaaaga tgctgaagat cagttgggtg cacgagtggg ttacatcgaa   3240
ctggatctca acagcggtaa gatccttgag agttttcgcc ccgaagaacg ttttccaatg   3300
atgagcactt ttaaagttct gctatgtggc gcggtattat cccgtattga cgccgggcaa   3360
gagcaactcg gtcgccgcat acactattct cagaatgact tggttgagta ctcaccagtc   3420
acagaaaagc atcttacgga tggcatgaca gtaagagaat tatgcagtgc tgccataacc   3480
atgagtgata acactgcggc caacttactt ctgacaacga tcggaggacc gaaggagcta   3540
accgcttttt tgcacaacat gggggatcat gtaactcgcc ttgatcgttg ggaaccggag   3600
ctgaatgaag ccataccaaa cgacgagcgt gacaccacga tgcctgtagc aatggcaaca   3660
acgttgcgca aactattaac tggcgaacta cttactctag cttcccggca acaattaata   3720
gactggatgg aggcggataa agttgcagga ccacttctgc gctcggccct tccggctggc   3780
tggtttattg ctgataaatc tggagccggt gagcgtgggt ctcgcggtat cattgcagca   3840
ctggggccag atggtaagcc ctcccgtatc gtagttatct acacgacggg gagtcaggca   3900
actatggatg aacgaaatag acagatcgct gagataggtg cctcactgat taagcattgg   3960
taactgtcag accaagttta ctcatatata ctttagattg atttaaaact tcatttttaa   4020
tttaaaagga tctaggtgaa gatccttttt gataatctca tgaccaaaat cccttaacgt   4080
gagttttcgt tccactgagc gtcagacccc gtagaaaaga tcaaaggatc ttcttgagat   4140
cctttttttc tgcgcgtaat ctgctgcttg caaacaaaaa aaccaccgct accagcggtg   4200
gtttgtttgc cggatcaaga gctaccaact ctttttccga aggtaactgg cttcagcaga   4260
gcgcagatac caaatactgt tcttctagtg tagccgtagt taggccacca cttcaagaac   4320
tctgtagcac cgcctacata cctcgctctg ctaatcctgt taccagtggc tgctgccagt   4380
ggcgataagt cgtgtcttac cgggttggac tcaagacgat agttaccgga taaggcgcag   4440
cggtcgggct gaacgggggg ttcgtgcaca cagcccagct tggagcgaac gacctacacc   4500
gaactgagat acctacagcg tgagctatga gaaagcgcca cgcttcccga agggagaaag   4560
gcggacaggt atccggtaag cggcagggtc ggaacaggag agcgcacgag ggagcttcca   4620
```

-continued

```
gggggaaacg cctggtatct ttatagtcct gtcgggtttc gccacctctg acttgagcgt   4680

cgatttttgt gatgctcgtc aggggggcgg agcctatgga aaaacgccag caacgcggcc   4740

tttttacggt tcctggcctt ttgctggcct tttgctcaca tgttctttcc tgcgttatcc   4800

cctgattctg tggataaccg tattaccgcc ttacgcgtgt aaaacgacgg ccagtagatc   4860

tgtaatacga ctcactatag ggcgctagct gctcgccgca gccgaacgac cgagcgcagc   4920

gagtcagtga gcgaggaa                                                   4938
```

<210> SEQ ID NO 2
<211> LENGTH: 4894
<212> TYPE: DNA
<213> ORGANISM: Artificial Sequence
<220> FEATURE:
<223> OTHER INFORMATION: Synthetic Vector

<400> SEQUENCE: 2

```
tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggag tatttacggt aaactgccca cttggcagta catcaagtgt atcatatgcc    240

aagtacgccc cctattgacg tcaatgacgg taaatggccc gcctggcatt atgcccagta    300

catgacctta tgggactttc ctacttggca gtacatctac gtattagtca tcgctattac    360

catggtgatg cggttttggc agtacatcaa tgggcgtgga tagcggtttg actcacgggg    420

atttccaagt ctccacccca ttgacgtcaa tgggagtttg ttttggcacc aaaatcaacg    480

ggactttcca aaatgtcgta acaactccgc cccattgacg caaatgggcg gtaggcgtgt    540

acggtgggag gtctatataa gcagagctgg tttagtgaac cgtcagatcc gctagcataa    600

cttcgtatag catacattat acgaagttat agatccaata ttattgaagc atttatcagg    660

gttattgtct catgagcgga tacatatttg aatgtattta gaaaaataaa caaatagggg    720

ttccgcgcac atttccccga aaagtgccac ctgacgtgga tctcgagctc aagcttcgaa    780

ttcagggttt ccttgacaat atcatactta tcctgtccct ttttttttcca cagctaccgg    840

tcgcgagcaa gggcgaggag ctgttcaccg gggtggtgcc catcctggtc gagctggacg    900

gcgacgtaaa cggccacaag ttcagcgtgt ccggcgaggg cgagggcgat gccacctacg    960

gcaagctgac cctgaagttc atctgcacca ccggcaagct gcccgtgccc tggcccaccc   1020

tcgtgaccac cctgacctac ggcgtgcagt gcttcagccg ctaccccgac cacatgaagc   1080

agcacgactt cttcaagtcc gccatgcccg aaggctacgt ccaggagcgc accatcttct   1140

tcaaggacga cggcaactac aagacccgcg ccgaggtgaa gttcgagggc gacaccctgg   1200

tgaaccgcat cgagctgaag ggcatcgact tcaaggagga cggcaacatc ctggggcaca   1260

agctggagta caactacaac agccacaacg tctatatcat ggccgacaag cagaagaacg   1320

gcatcaaggt gaacttcaag atccgccaca acatcgagga cggcagcgtg cagctcgccg   1380

accactacca gcagaacacc cccatcggcg acggccccgt gctgctgccc gacaaccact   1440

acctgagcac ccagtccgcc ctgagcaaag accccaacga gaagcgcgat cacatggtcc   1500

tgctggagtt cgtgaccgcc gccgggatca ctctcggcat ggacgagctg tacaagtaaa   1560

gcggccgcga ctctagatca taatcagcca taccacattt gtagaggttt tacttgcttt   1620

aaaaaacctc ccacacctcc ccctgaacct gaaacataaa atgaatgcaa ttgttgttgt   1680

taacttgttt attgcagctt ataatggtta caaataaagc aatagcatca caaatttcac   1740
```

-continued

```
aaataaagca ttttttcac tgcattctag ttgtggtttg tccaaactca tcaatgtatc   1800
ttaaggcgta aattgtaagc gttaatattt tgttaaaatt cgcgttaaat ttttgttaaa  1860
tcagctcatt ttttaaccaa taggccgaaa tcggcaaaat cccttataaa tcaaaagaat  1920
agaccgagat agggttgagt gttgttccag tttggaacaa gagtccacta ttaaagaacg  1980
tggactccaa cgtcaaaggg cgaaaaaccg tctatcaggg cgatggccca ctacgtgaac  2040
catcacccta atcaagtttt ttggggtcga ggtgccgtaa agcactaaat cggaacccta  2100
aagggagccc ccgatttaga gcttgacggg gaaagccggc gaacgtggcg agaaaggaag  2160
ggaagaaagc gaaaggagcg ggcgctaggg cgctggcaag tgtagcggtc acgctgcgcg  2220
taaccaccac acccgccgcg cttaatgcgc cgctacaggg cgcgtcaggt ggcacttttc  2280
ggggaaatgt gcgcggaacc cctatttgtt tatttttcta aatacattca aatatgtatc  2340
cgctcatgag acaataaccc tgataaatgc ttcaataata ttgaaaaagg aagagtcctg  2400
aggcggaaag aaccagctgt ggaatgtgtg tcagttaggg tgtggaaagt ccccaggctc  2460
cccagcaggc agaagtatgc aaagcatgca tctcaattag tcagcaacca ggtgtggaaa  2520
gtccccaggc tccccagcag gcagaagtat gcaaagcatg catctcaatt agtcagcaac  2580
catagtcccg cccctaactc cgcccatccc gcccctaact ccgcccagtt ccgcccattc  2640
tccgccccat ggctgactaa ttttttttat ttatgcagag gccgaggccg cctcggcctc  2700
tgagctattc cagaagtagt gaggaggctt ttttggaggc ctaggctttt gcaaagatcg  2760
atcaagagac aggatgagga tcgtttcgca tgattgaaca agatggattg cacgcaggtt  2820
ctccggccgc ttgggtggag aggctattcg gctatgactg ggcacaacag acaatcggct  2880
gctctgatgc cgccgtgttc cggctgtcag cgcaggggcg cccggttctt tttgtcaaga  2940
ccgacctgtc cggtgccctg aatgaactgc aagacgaggc agcgcggcta tcgtggctgg  3000
ccacgacggg cgttccttgc gcagctgtgc tcgacgttgt cactgaagcg ggaagggact  3060
ggctgctatt gggcgaagtg ccggggcagg atctcctgtc atctcacctt gctcctgccg  3120
agaaagtatc catcatggct gatgcaatgc ggcggctgca tacgcttgat ccggctacct  3180
gcccattcga ccaccaagcg aaacatcgca tcgagcgagc acgtactcgg atggaagccg  3240
gtcttgtcga tcaggatgat ctggacgaag agcatcaggg gctcgcgcca gccgaactgt  3300
tcgccaggct caaggcgagc atgcccgacg gcgaggatct cgtcgtgacc catggcgatg  3360
cctgcttgcc gaatatcatg gtggaaaatg gccgcttttc tggattcatc gactgtggcc  3420
ggctgggtgt ggcggaccgc tatcaggaca tagcgttggc tacccgtgat attgctgaag  3480
agcttggcgg cgaatgggct gaccgcttcc tcgtgcttta cggtatcgcc gctcccgatt  3540
cgcagcgcat cgccttctat cgccttcttg acgagttctt ctgagcggga ctctggggtt  3600
cgaaatgacc gaccaagcga cgcccaacct gccatcacga gatttcgatt ccaccgccgc  3660
cttctatgaa aggttgggct tcggaatcgt tttccgggac gccggctgga tgatcctcca  3720
gcgcggggat ctcatgctgg agttcttcgc ccaccctagg gggaggctaa ctgaaacacg  3780
gaaggagaca ataccggaag gaacccgcgc tatgacggca ataaaaagac agaataaaac  3840
gcacggtgtt gggtcgtttg ttcataaacg cggggttcgg tcccagggct ggcactctgt  3900
cgataccca ccgagacccc attggggcca atacgcccgc gtttcttcct tttccccacc  3960
ccaccccca agttcgggtg aaggcccagg gctcgcagcc aacgtcgggg cggcaggccc  4020
tgccatagcc tcaggttact catatatact ttagattgat ttaaaacttc atttttaatt  4080
```

-continued

```
taaaaggatc taggtgaaga tcctttttga taatctcatg accaaaatcc cttaacgtga   4140
gttttcgttc cactgagcgt cagaccccgt agaaaagatc aaaggatctt cttgagatcc   4200
tttttttctg cgcgtaatct gctgcttgca aacaaaaaaa ccaccgctac cagcggtggt   4260
ttgtttgccg gatcaagagc taccaactct ttttccgaag gtaactggct tcagcagagc   4320
gcagatacca aatactgtcc ttctagtgta gccgtagtta ggccaccact tcaagaactc   4380
tgtagcaccg cctacatacc tcgctctgct aatcctgtta ccagtggctg ctgccagtgg   4440
cgataagtcg tgtcttaccg ggttggactc aagacgatag ttaccggata aggcgcagcg   4500
gtcgggctga acggggggtt cgtgcacaca gcccagcttg gagcgaacga cctacaccga   4560
actgagatac ctacagcgtg agctatgaga aagcgccacg cttcccgaag ggagaaaggc   4620
ggacaggtat ccggtaagcg gcagggtcgg aacaggagag cgcacgaggg agcttccagg   4680
gggaaacgcc tggtatcttt atagtcctgt cgggtttcgc cacctctgac ttgagcgtcg   4740
atttttgtga tgctcgtcag gggggcggag cctatggaaa aacgccagca acgcggcctt   4800
tttacggttc ctggcctttt gctggccttt tgctcacatg ttctttcctg cgttatcccc   4860
tgattctgtg gataaccgta ttaccgccat gcat                                4894
```

<210> SEQ ID NO 3
<211> LENGTH: 6525
<212> TYPE: DNA
<213> ORGANISM: Artificial Sequence
<220> FEATURE:
<223> OTHER INFORMATION: Synthetic Vector

<400> SEQUENCE: 3

```
gcggccgcat aacttcgtat agcatacatt atacgaagtt atcagtcgac accatggaag     60
acgccaaaaa cataaagaaa ggcccggcgc cattctatcc tctagaggat ggaaccgctg    120
gagagcaact gcataaggct atgaagagat acgccctggt tcctggaaca attgctttta    180
cagatgcaca tatcgaggtg aacatcacgt acgcggaata cttcgaaatg tccgttcggt    240
tggcagaagc tatgaaacga tatgggctga atacaaatca cagaatcgtc gtatgcagtg    300
aaaactctct tcaattcttt atgccggtgt tgggcgcgtt atttatcgga gttgcagttg    360
cgcccgcgaa cgacatttat aatgaacgtg aattgctcaa cagtatgaac atttcgcagc    420
ctaccgtagt gtttgtttcc aaaaaggggt tgcaaaaaat tttgaacgtg caaaaaaaat    480
taccaataat tcagaaaatt attatcatgg attctaaaac ggattaccag ggatttcagt    540
cgatgtacac gttcgtcaca tctcatctac ctcccggttt taatgagtac gattttgtac    600
cagagtcctt tgatcgtgac aaaacaattg cactgataat gaattcctct ggatctactg    660
ggttacctaa gggtgtggcc cttccgcata gaactgcctg cgtcagattc tcgcatgcca    720
gagatcctat ttttggcaat caaatcattc cggatactgc gattttaagt gttgttccat    780
tccatcacgg ttttggaatg tttactacac tcggatattt gatatgtgga tttcgagtcg    840
tcttaatgta tagatttgaa gaagagctgt ttttacgatc ccttcaggat tacaaaattc    900
aaagtgcgtt gctagtacca accctatttt cattcttcgc caaaagcact ctgattgaca    960
aatacgattt atctaattta cacgaaattg cttctggggg cgcacctctt tcgaaagaag   1020
tcggggaagc ggttgcaaaa cgcttccatc ttccagggat acgacaagga tatgggctca   1080
ctgagactac atcagctatt ctgattacac ccgaggggga tgataaaccg ggcgcggtcg   1140
gtaaagttgt tccatttttt gaagcgaagg ttgtggatct ggataccggg aaaacgctgg   1200
gcgttaatca gagaggcgaa ttatgtgtca gaggacctat gattatgtcc ggttatgtaa   1260
```

-continued

```
acaatccgga agcgaccaac gccttgattg acaaggatgg atggctacat tctggagaca   1320
tagcttactg ggacgaagac gaacacttct tcatagttga ccgcttgaag tctttaatta   1380
aatacaaagg atatcaggtg gcccccgctg aattggaatc gatattgtta caacacccca   1440
acatcttcga cgcgggcgtg gcaggtcttc ccgacgatga cgccggtgaa cttcccgccg   1500
ccgttgttgt tttggagcac ggaaagacga tgacggaaaa agagatcgtg gattacgtcg   1560
ccagtcaagt aacaaccgcg aaaaagttgc gcggaggagt tgtgtttgtg gacgaagtac   1620
cgaaaggtct taccggaaaa ctcgacgcaa gaaaaatcag agagatcctc ataaaggcca   1680
agaagggcgg aaagtccaaa ttgaggatcc gggcccaggt gagtggtcat aatcataatc   1740
ataatcataa tcataatcac aactagccta ggagatcctg gtcatgacta gtgcttggat   1800
tctcaccaat aaaaaacgcc cggcggcaac cgagcgttct gaacaaatcc agatggagtt   1860
ctgaggtcat tactggatct atcaacagga gtccaagcga gctcgatatc aaattacgcc   1920
ccgccctgcc actcatcgca gtactgttgt aattcattaa gcattctgcc gacatggaag   1980
ccatcacaaa cggcatgatg aacctgaatc gccagcggca tcagcacctt gtcgccttgc   2040
gtataatatt tgcccatggt gaaaacgggg gcgaagaagt tgtccatatt ggccacgttt   2100
aaatcaaaac tggtgaaact cacccaggga ttggctgaga cgaaaaacat attctcaata   2160
aaccctttag ggaaataggc caggttttca ccgtaacacg ccacatcttg cgaatatatg   2220
tgtagaaact gccggaaatc gtcgtggtat tcactccaga gcgatgaaaa cgtttcagtt   2280
tgctcatgga aaacggtgta acaagggtga acactatccc atatcaccag ctcaccgtct   2340
ttcattgcca tacgaaattc cggatgagca ttcatcaggc gggcaagaat gtgaataaag   2400
gccggataaa acttgtgctt atttttcttt acggtcttta aaaaggccgt aatatccagc   2460
tgaacggtct ggttataggt acattgagca actgactgaa atgcctcaaa atgttcttta   2520
cgatgccatt gggatatatc aacggtggta tatccagtga tttttttctc cattttagct   2580
tccttagctc ctgaaagatc cataacttcg tatagcatac attatacgaa gttatgcggc   2640
cgcgacgtcc acatatacct gccgttcact attatttagt gaaatgagat attatgatat   2700
tttctgaatt gtgattaaaa aggcaacttt atgcccatgc aacagaaact ataaaaaata   2760
cagagaatga aaagaaacag atagattttt tagttcttta ggcccgtagt ctgcaaatcc   2820
ttttatgatt ttctatcaaa caaaagagga aaatagacca gttgcaatcc aaacgagagt   2880
ctaatagaat gaggtcgaaa agtaaatcgc gcgggtttgt tactgataaa gcaggcaaga   2940
cctaaaatgt gtaaagggca aagtgtatac tttggcgtca ccccttacat attttaggtc   3000
tttttttatt gtgcgtaact aacttgccat cttcaaacag gagggctgga agaagcagac   3060
cgctaacaca gtacataaaa aaggagacat gaacgatgaa catcaaaaag tttgcaaaac   3120
aagcaacagt attaaccttt actaccgcac tgctggcagg aggcgcaact caagcgtttg   3180
cgaaagaaac gaaccaaaag ccatataagg aaacatacgg catttcccat attacacgcc   3240
atgatatgct gcaaatccct gaacagcaaa aaaatgaaaa atatcaagtt cctgagttcg   3300
attcgtccac aattaaaaat atctcttctg caaaaggcct ggacgtttgg gacagctggc   3360
cattacaaaa cgctgacggc actgtcgcaa actatcacgg ctaccacatc gtctttgcat   3420
tagccggaga tcctaaaaat gcggatgaca catcgattta catgttctat caaaaagtcg   3480
gcgaaacttc tattgacagc tggaaaaacg ctggccgcgt ctttaaagac agcgacaaat   3540
tcgatgcaaa tgattctatc ctaaaagacc aaacacaaga atggtcaggt tcagccacat   3600
```

-continued

```
ttacatctga cggaaaaatc cgtttattct acactgattt ctccggtaaa cattacggca   3660
aacaaacact gacaactgca caagttaacg tatcagcatc agacagctct ttgaacatca   3720
acggtgtaga ggattataaa tcaatctttg acggtgacgg aaaaacgtat caaaatgtac   3780
agcagttcat cgatgaaggc aactacagct caggcgacaa ccatacgctg agagatcctc   3840
actacgtaga agataaaggc cacaaatact tagtatttga agcaaacact ggaactgaag   3900
atggctacca aggcgaagaa tctttattta acaaagcata ctatggcaaa agcacatcat   3960
tcttccgtca agaaagtcaa aaacttctgc aaagcgataa aaaacgcacg gctgagttag   4020
caaacggcgc tctcggtatg attgagctaa acgatgatta cacactgaaa aaagtgatga   4080
aaccgctgat tgcatctaac acagtaacag atgaaattga acgcgcgaac gtctttaaaa   4140
tgaacggcaa atggtacctg ttcactgact cccgcggatc aaaaatgacg attgacggca   4200
ttacgtctaa cgatatttac atgcttggtt atgtttctaa ttctttaact ggcccataca   4260
agccgctgaa caaaactggc cttgtgttaa aaatggatct tgatcctaac gatgtaacct   4320
ttacttactc acacttcgct gtacctcaag cgaaaggaaa caatgtcgtg attacaagct   4380
atatgacaaa cagaggattc tacgcagaca aacaatcaac gtttgcgcct agcttcctgc   4440
tgaacatcaa aggcaagaaa acatctgttg tcaaagacag catccttgaa caaggacaat   4500
taacagttaa caaataaaaa cgcaaaagaa aatgccgata tcctattggc attgacgtca   4560
ggtggcactt ttcggggaaa tgtgcgcgga acccctattt gtttattttt ctaaatacat   4620
tcaaatatgt atccgctcat gagacaataa ccctgataaa tgcttcaata atattgaaaa   4680
aggaagagta tgagtattca acatttccgt gtcgccctta ttcccttttt tgcggcattt   4740
tgccttcctg tttttgctca cccagaaacg ctggtgaaag taaaagatgc tgaagatcag   4800
ttgggtgcac gagtgggtta catcgaactg gatctcaaca gcggtaagat ccttgagagt   4860
tttcgccccg aagaacgttt tccaatgatg agcactttta aagttctgct atgtggcgcg   4920
gtattatccc gtattgacgc cgggcaagag caactcggtc gccgcataca ctattctcag   4980
aatgacttgg ttgagtactc accagtcaca gaaaagcatc ttacggatgg catgacagta   5040
agagaattat gcagtgctgc cataaccatg agtgataaca ctgcggccaa cttacttctg   5100
acaacgatcg gaggaccgaa ggagctaacc gcttttttgc acaacatggg ggatcatgta   5160
actcgccttg atcgttggga accggagctg aatgaagcca taccaaacga cgagcgtgac   5220
accacgatgc ctgtagcaat ggcaacaacg ttgcgcaaac tattaactgg cgaactactt   5280
actctagctt cccggcaaca attaatagac tggatggagg cggataaagt tgcaggacca   5340
cttctgcgct cggcccttcc ggctggctgg tttattgctg ataaatctgg agccggtgag   5400
cgtgggtctc gcggtatcat tgcagcactg gggccagatg gtaagccctc ccgtatcgta   5460
gttatctaca cgacggggag tcaggcaact atggatgaac gaaatagaca gatcgctgag   5520
ataggtgcct cactgattaa gcattggtaa ctgtcagacc aagtttactc atatatactt   5580
tagattgatt taaaacttca tttttaattt aaaaggatct aggtgaagat cctttttgat   5640
aatctcatga ccaaaatccc ttaacgtgag ttttcgttcc actgagcgtc agaccccgta   5700
gaaaagatca aaggatcttc ttgagatcct ttttttctgc gcgtaatctg ctgcttgcaa   5760
acaaaaaaac caccgctacc agcggtggtt tgtttgccgg atcaagagct accaactctt   5820
tttccgaagg taactggctt cagcagagcg cagataccaa atactgttct tctagtgtag   5880
ccgtagttag gccaccactt caagaactct gtagcaccgc ctacatacct cgctctgcta   5940
atcctgttac cagtggctgc tgccagtggc gataagtcgt gtcttaccgg gttggactca   6000
```

-continued

```
agacgatagt taccggataa ggcgcagcgg tcgggctgaa cggggggttc gtgcacacag   6060

cccagcttgg agcgaacgac ctacaccgaa ctgagatacc tacagcgtga gctatgagaa   6120

agcgccacgc ttcccgaagg gagaaaggcg gacaggtatc cggtaagcgg cagggtcgga   6180

acaggagagc gcacgaggga gcttccaggg ggaaacgcct ggtatcttta tagtcctgtc   6240

gggtttcgcc acctctgact tgagcgtcga tttttgtgat gctcgtcagg ggggcggagc   6300

ctatggaaaa acgccagcaa cgcggccttt ttacggttcc tggccttttg ctggcctttt   6360

gctcacatgt tctttcctgc gttatcccct gattctgtgg ataaccgtat taccgcctta   6420

cgcgtgtaaa acgacggcca gtagatctgt aatacgactc actatagggc gctagctgct   6480

cgccgcagcc gaacgaccga gcgcagcgag tcagtgagcg aggaa                   6525
```

```
<210> SEQ ID NO 4
<211> LENGTH: 7487
<212> TYPE: DNA
<213> ORGANISM: Artificial Sequence
<220> FEATURE:
<223> OTHER INFORMATION: Synthetic Vector

<400> SEQUENCE: 4

tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggag tatttacggt aaactgccca cttggcagta catcaagtgt atcatatgcc    240

aagtacgccc cctattgacg tcaatgacgg taaatggccc gcctggcatt atgcccagta    300

catgacctta tgggactttc ctacttggca gtacatctac gtattagtca tcgctattac    360

catggtgatg cggttttggc agtacatcaa tgggcgtgga tagcggtttg actcacgggg    420

atttccaagt ctccacccca ttgacgtcaa tgggagtttg ttttggcacc aaaatcaacg    480

ggactttcca aaatgtcgta acaactccgc cccattgacg caaatgggcg gtaggcgtgt    540

acggtgggag gtctatataa gcagagctgg tttagtgaac cgtcagatcc gctagcataa    600

cttcgtatag catacattat acgaagttat cagtcgacac catggaagac gccaaaaaca    660

taaagaaagg cccggcgcca ttctatcctc tagaggatgg aaccgctgga gagcaactgc    720

ataaggctat gaagagatac gccctggttc ctggaacaat tgcttttaca gatgcacata    780

tcgaggtgaa catcacgtac gcggaatact tcgaaatgtc cgttcggttg gcagaagcta    840

tgaaacgata tgggctgaat acaaatcaca gaatcgtcgt atgcagtgaa aactctcttc    900

aattctttat gccggtgttg ggcgcgttat ttatcggagt tgcagttgcg cccgcgaacg    960

acatttataa tgaacgtgaa ttgctcaaca gtatgaacat ttcgcagcct accgtagtgt   1020

ttgtttccaa aaaggggttg caaaaaattt tgaacgtgca aaaaaaatta ccaataattc   1080

agaaaattat tatcatggat tctaaaacgg attaccaggg atttcagtcg atgtacacgt   1140

tcgtcacatc tcatctacct cccggtttta atgagtacga ttttgtacca gagtcctttg   1200

atcgtgacaa aacaattgca ctgataatga attcctctgg atctactggg ttacctaagg   1260

gtgtggccct tccgcataga actgcctgcg tcagattctc gcatgccaga gatcctattt   1320

ttggcaatca aatcattccg gatactgcga ttttaagtgt tgttccattc catcacggtt   1380

ttggaatgtt tactacactc ggatatttga tatgtggatt tcgagtcgtc ttaatgtata   1440

gatttgaaga agagctgttt ttacgatccc ttcaggatta caaaattcaa agtgcgttgc   1500
```

-continued

```
tagtaccaac cctattttca ttcttcgcca aaagcactct gattgacaaa tacgatttat   1560
ctaatttaca cgaaattgct tctgggggcg cacctctttc gaaagaagtc ggggaagcgg   1620
ttgcaaaacg cttccatctt ccagggatac gacaaggata tgggctcact gagactacat   1680
cagctattct gattacaccc gagggggatg ataaaccggg cgcggtcggt aaagttgttc   1740
catttttga agcgaaggtt gtggatctgg ataccgggaa aacgctgggc gttaatcaga   1800
gaggcgaatt atgtgtcaga ggacctatga ttatgtccgg ttatgtaaac aatccggaag   1860
cgaccaacgc cttgattgac aaggatggat ggctacattc tggagacata gcttactggg   1920
acgaagacga acacttcttc atagttgacc gcttgaagtc tttaattaaa tacaaaggat   1980
atcaggtggc ccccgctgaa ttggaatcga tattgttaca acaccccaac atcttcgacg   2040
cgggcgtggc aggtcttccc gacgatgacg ccggtgaact tcccgccgcc gttgttgttt   2100
tggagcacgg aaagacgatg acggaaaaag agatcgtgga ttacgtcgcc agtcaagtaa   2160
caaccgcgaa aaagttgcgc ggaggagttg tgtttgtgga cgaagtaccg aaaggtctta   2220
ccggaaaact cgacgcaaga aaaatcagag agatcctcat aaaggccaag aagggcggaa   2280
agtccaaatt gaggatccgg gcccaggtga gtggtcataa tcataatcat aatcataatc   2340
ataatcacaa ctagcctagg agatcctggt catgactagt gcttggattc tcaccaataa   2400
aaaacgcccg gcggcaaccg agcgttctga acaaatccag atggagttct gaggtcatta   2460
ctggatctat caacaggagt ccaagcgagc tcgatatcaa attacgcccc gccctgccac   2520
tcatcgcagt actgttgtaa ttcattaagc attctgccga catggaagcc atcacaaacg   2580
gcatgatgaa cctgaatcgc cagcggcatc agcaccttgt cgccttgcgt ataatatttg   2640
cccatggtga aaacgggggc gaagaagttg tccatattgg ccacgtttaa atcaaaactg   2700
gtgaaactca cccagggatt ggctgagacg aaaaacatat tctcaataaa ccctttaggg   2760
aaataggcca ggttttcacc gtaacacgcc acatcttgcg aatatatgtg tagaaactgc   2820
cggaaatcgt cgtggtattc actccagagc gatgaaaacg tttcagtttg ctcatggaaa   2880
acggtgtaac aagggtgaac actatcccat atcaccagct caccgtcttt cattgccata   2940
cgaaattccg gatgagcatt catcaggcgg gcaagaatgt gaataaaggc cggataaaac   3000
ttgtgcttat ttttctttac ggtctttaaa aaggccgtaa tatccagctg aacggtctgg   3060
ttataggtac attgagcaac tgactgaaat gcctcaaaat gttctttacg atgccattgg   3120
gatatatcaa cggtggtata tccagtgatt tttttctcca ttttagcttc cttagctcct   3180
gaaagatcca taacttcgta tagcatacat tatacgaagt tatagatcca atattattga   3240
agcatttatc agggttattg tctcatgagc ggatacatat ttgaatgtat ttagaaaaat   3300
aaacaaatag gggttccgcg cacatttccc cgaaaagtgc cacctgacgt ggatctcgag   3360
ctcaagcttc gaattcaggg tttccttgac aatatcatac ttatcctgtc cctttttttt   3420
ccacagctac cggtcgcgag caagggcgag gagctgttca ccggggtggt gcccatcctg   3480
gtcgagctgg acggcgacgt aaacggccac aagttcagcg tgtccggcga gggcgagggc   3540
gatgccacct acggcaagct gaccctgaag ttcatctgca ccaccggcaa gctgcccgtg   3600
ccctggccca ccctcgtgac caccctgacc tacggcgtgc agtgcttcag ccgctacccc   3660
gaccacatga agcagcacga cttcttcaag tccgccatgc ccgaaggcta cgtccaggag   3720
cgcaccatct tcttcaagga cgacggcaac tacaagaccc gcgccgaggt gaagttcgag   3780
ggcgacaccc tggtgaaccg catcgagctg aagggcatcg acttcaagga ggacggcaac   3840
atcctggggc acaagctgga gtacaactac aacagccaca acgtctatat catggccgac   3900
```

-continued

```
aagcagaaga acggcatcaa ggtgaacttc aagatccgcc acaacatcga ggacggcagc   3960
gtgcagctcg ccgaccacta ccagcagaac acccccatcg gcgacggccc cgtgctgctg   4020
cccgacaacc actacctgag cacccagtcc gccctgagca aagaccccaa cgagaagcgc   4080
gatcacatgg tcctgctgga gttcgtgacc gccgccggga tcactctcgg catggacgag   4140
ctgtacaagt aaagcggccg cgactctaga tcataatcag ccataccaca tttgtagagg   4200
ttttacttgc tttaaaaaac ctcccacacc tccccctgaa cctgaaacat aaaatgaatg   4260
caattgttgt tgttaacttg tttattgcag cttataatgg ttacaaataa agcaatagca   4320
tcacaaattt cacaaataaa gcattttttt cactgcattc tagttgtggt ttgtccaaac   4380
tcatcaatgt atcttaaggc gtaaattgta agcgttaata ttttgttaaa attcgcgtta   4440
aatttttgtt aaatcagctc attttttaac caataggccg aaatcggcaa aatcccttat   4500
aaatcaaaag aatagaccga gatagggttg agtgttgttc cagtttggaa caagagtcca   4560
ctattaaaga acgtggactc caacgtcaaa gggcgaaaaa ccgtctatca gggcgatggc   4620
ccactacgtg aaccatcacc ctaatcaagt tttttggggt cgaggtgccg taaagcacta   4680
aatcggaacc ctaaagggag cccccgattt agagcttgac ggggaaagcc ggcgaacgtg   4740
gcgagaaagg aagggaagaa agcgaaagga gcgggcgcta gggcgctggc aagtgtagcg   4800
gtcacgctgc gcgtaaccac cacacccgcc gcgcttaatg cgccgctaca gggcgcgtca   4860
ggtggcactt ttcggggaaa tgtgcgcgga acccctattt gtttattttt ctaaatacat   4920
tcaaatatgt atccgctcat gagacaataa ccctgataaa tgcttcaata atattgaaaa   4980
aggaagagtc ctgaggcgga aagaaccagc tgtggaatgt gtgtcagtta gggtgtggaa   5040
agtccccagg ctccccagca ggcagaagta tgcaaagcat gcatctcaat tagtcagcaa   5100
ccaggtgtgg aaagtcccca ggctccccag caggcagaag tatgcaaagc atgcatctca   5160
attagtcagc aaccatagtc ccgcccctaa ctccgcccat cccgccccta actccgccca   5220
gttccgccca ttctccgccc catggctgac taattttttt tatttatgca gaggccgagg   5280
ccgcctcggc ctctgagcta ttccagaagt agtgaggagg cttttttgga ggcctaggct   5340
tttgcaaaga tcgatcaaga gacaggatga ggatcgtttc gcatgattga acaagatgga   5400
ttgcacgcag gttctccggc cgcttgggtg gagaggctat tcggctatga ctgggcacaa   5460
cagacaatcg gctgctctga tgccgccgtg ttccggctgt cagcgcaggg gcgcccggtt   5520
ctttttgtca agaccgacct gtccggtgcc ctgaatgaac tgcaagacga ggcagcgcgg   5580
ctatcgtggc tggccacgac gggcgttcct tgcgcagctg tgctcgacgt tgtcactgaa   5640
gcgggaaggg actggctgct attgggcgaa gtgccggggc aggatctcct gtcatctcac   5700
cttgctcctg ccgagaaagt atccatcatg gctgatgcaa tgcggcggct gcatacgctt   5760
gatccggcta cctgcccatt cgaccaccaa gcgaaacatc gcatcgagcg agcacgtact   5820
cggatggaag ccggtcttgt cgatcaggat gatctggacg aagagcatca ggggctcgcg   5880
ccagccgaac tgttcgccag gctcaaggcg agcatgcccg acggcgagga tctcgtcgtg   5940
acccatggcg atgcctgctt gccgaatatc atggtggaaa atggccgctt ttctggattc   6000
atcgactgtg gccggctggg tgtggcggac cgctatcagg acatagcgtt ggctacccgt   6060
gatattgctg aagagcttgg cggcgaatgg gctgaccgct tcctcgtgct ttacggtatc   6120
gccgctcccg attcgcagcg catcgccttc tatcgccttc ttgacgagtt cttctgagcg   6180
ggactctggg gttcgaaatg accgaccaag cgacgcccaa cctgccatca cgagatttcg   6240
```

-continued

```
attccaccgc cgccttctat gaaaggttgg gcttcggaat cgttttccgg gacgccggct   6300
ggatgatcct ccagcgcggg gatctcatgc tggagttctt cgcccaccct agggggaggc   6360
taactgaaac acggaaggag acaataccgg aaggaacccg cgctatgacg gcaataaaaa   6420
gacagaataa aacgcacggt gttgggtcgt ttgttcataa acgcggggtt cggtcccagg   6480
gctggcactc tgtcgatacc ccaccgagac cccattgggg ccaatacgcc cgcgtttctt   6540
ccttttcccc accccacccc ccaagttcgg gtgaaggccc agggctcgca gccaacgtcg   6600
gggcggcagg ccctgccata gcctcaggtt actcatatat actttagatt gatttaaaac   6660
ttcattttta atttaaaagg atctaggtga agatcctttt tgataatctc atgaccaaaa   6720
tcccttaacg tgagttttcg ttccactgag cgtcagaccc cgtagaaaag atcaaaggat   6780
cttcttgaga tccttttttt ctgcgcgtaa tctgctgctt gcaaacaaaa aaaccaccgc   6840
taccagcggt ggtttgtttg ccggatcaag agctaccaac tctttttccg aaggtaactg   6900
gcttcagcag agcgcagata ccaaatactg tccttctagt gtagccgtag ttaggccacc   6960
acttcaagaa ctctgtagca ccgcctacat acctcgctct gctaatcctg ttaccagtgg   7020
ctgctgccag tggcgataag tcgtgtctta ccgggttgga ctcaagacga tagttaccgg   7080
ataaggcgca gcggtcgggc tgaacggggg gttcgtgcac acagcccagc ttggagcgaa   7140
cgacctacac cgaactgaga tacctacagc gtgagctatg agaaagcgcc acgcttcccg   7200
aagggagaaa ggcggacagg tatccggtaa gcggcagggt cggaacagga gagcgcacga   7260
gggagcttcc agggggaaac gcctggtatc tttatagtcc tgtcgggttt cgccacctct   7320
gacttgagcg tcgatttttg tgatgctcgt caggggggcg gagcctatgg aaaaacgcca   7380
gcaacgcggc ctttttacgg ttcctggcct tttgctggcc ttttgctcac atgttctttc   7440
ctgcgttatc ccctgattct gtggataacc gtattaccgc catgcat                  7487
```

<210> SEQ ID NO 5
<211> LENGTH: 39
<212> TYPE: DNA
<213> ORGANISM: Artificial Sequence
<220> FEATURE:
<223> OTHER INFORMATION: splice sequence

<400> SEQUENCE: 5

```
caggtgagtt aggtaagtga acatggtcat agctgtttc                           39
```

<210> SEQ ID NO 6
<211> LENGTH: 47
<212> TYPE: DNA
<213> ORGANISM: Artificial Sequence
<220> FEATURE:
<223> OTHER INFORMATION: splice sequence

<400> SEQUENCE: 6

```
ccgggtccac tcaatccatt cacttgtacc agtatcgaca aaggatc                   47
```

<210> SEQ ID NO 7
<211> LENGTH: 58
<212> TYPE: DNA
<213> ORGANISM: Artificial Sequence
<220> FEATURE:
<223> OTHER INFORMATION: splice sequence

<400> SEQUENCE: 7

```
aattcagggt ttccttgaca atatcatact tatcctgtcc cttttttttc cacagcta       58
```

<210> SEQ ID NO 8
<211> LENGTH: 58
<212> TYPE: DNA
<213> ORGANISM: Artificial Sequence
<220> FEATURE:
<223> OTHER INFORMATION: splice sequence

<400> SEQUENCE: 8
gtcccaaagg aactgttata gtatgaatag gacagggaaa aaaaaggtgt cgatggcc 58

<210> SEQ ID NO 9
<211> LENGTH: 50
<212> TYPE: DNA
<213> ORGANISM: Artificial Sequence
<220> FEATURE:
<223> OTHER INFORMATION: splice sequence

<400> SEQUENCE: 9
agttggtggt gaggccctgg gcaggttggt atcaaggtta caagacaggt 50

<210> SEQ ID NO 10
<211> LENGTH: 50
<212> TYPE: DNA
<213> ORGANISM: Artificial Sequence
<220> FEATURE:
<223> OTHER INFORMATION: splice sequence

<400> SEQUENCE: 10
tcaaccacca ctccgggacc cgtccaacca tagttccaat gttctgtcca 50

<210> SEQ ID NO 11
<211> LENGTH: 100
<212> TYPE: DNA
<213> ORGANISM: Artificial Sequence
<220> FEATURE:
<223> OTHER INFORMATION: splice sequence

<400> SEQUENCE: 11
cgtagtgtaa agttggtggt gaggccctgg gcaggttggt atcaaggtta caagacaggt 60
cataatcata atcataatca taatcataat cacaactagc 100

<210> SEQ ID NO 12
<211> LENGTH: 108
<212> TYPE: DNA
<213> ORGANISM: Artificial Sequence
<220> FEATURE:
<223> OTHER INFORMATION: splice sequence

<400> SEQUENCE: 12
ccgggcatca catttcaacc accactccgg gacccgtcca accatagttc caatgttctg 60
tccagtatta gtattagtat tagtattagt attagtgttg atcggatc 108

<210> SEQ ID NO 13
<211> LENGTH: 42
<212> TYPE: DNA
<213> ORGANISM: Artificial Sequence
<220> FEATURE:
<223> OTHER INFORMATION: splice sequence

<400> SEQUENCE: 13
ggtcataatc ataatcataa tcataatcat aatcacaact ag 42

<210> SEQ ID NO 14
<211> LENGTH: 42
<212> TYPE: DNA

-continued

```
<213> ORGANISM: Artificial Sequence
<220> FEATURE:
<223> OTHER INFORMATION: tag sequence

<400> SEQUENCE: 14

ccagtattag tattagtatt agtattagta ttagtgttga tc                      42


<210> SEQ ID NO 15
<211> LENGTH: 13
<212> TYPE: PRT
<213> ORGANISM: Artificial Sequence
<220> FEATURE:
<223> OTHER INFORMATION: tag sequence

<400> SEQUENCE: 15

Gly His Asn His Asn His Asn His Asn His Asn His Asn
 1               5                  10


<210> SEQ ID NO 16
<211> LENGTH: 91
<212> TYPE: DNA
<213> ORGANISM: Artificial Sequence
<220> FEATURE:
<223> OTHER INFORMATION: splice sequence

<400> SEQUENCE: 16

aattcttggg tttctgatag gcactgactc tctctgccga ttggtctatt ttcccaccct     60

taggctgctg gtggtctacc cttggaccct a                                  91


<210> SEQ ID NO 17
<211> LENGTH: 91
<212> TYPE: DNA
<213> ORGANISM: Artificial Sequence
<220> FEATURE:
<223> OTHER INFORMATION: splice sequence

<400> SEQUENCE: 17

gaacccaaag actatccgtg actgagagag acggctaacc agataaaagg gtgggaatcc     60

gacgaccacc agatgggaac ctgggatggc c                                  91
```

SEQUENCE SPECIFIC RECOMBINASE-BASED METHODS FOR PRODUCING INTRON CONTAINING VECTORS AND COMPOSITIONS FOR USE IN PRACTICING THE SAME

CROSS-REFERENCE TO RELATED APPLICATIONS

Pursuant to 35 U.S.C. §119(e), this application claims priority to the filing date of U.S. Provisional Patent Application Ser. No. 60/263,358 filed Jan. 18, 2001; the disclosure of which applications is herein incorporated by reference.

INTRODUCTION

1. Field of the Invention

The field of this invention is molecular biology, particularly recombinant DNA engineering.

2. Background of the Invention

The processes of isolating, cloning and expressing genes are central to the field of molecular biology and play prominent roles in research and industry in biotechnology and related fields. Until recently, the isolation and cloning of genes has been achieved in vitro using restriction endonucleases and DNA ligases. Restriction endonucleases are enzymes which recognize and cleave double-stranded DNA at a specific nucleotide sequence, and DNA ligases are enzymes which join fragments of DNA together via the phosphodiester bond. A DNA sequence of interest can be "cut" or digested into manageable pieces using a restriction endonuclease and then inserted into an appropriate vector for cloning using DNA ligase. However, in order to transfer the DNA of interest into a different vector—most often a specialized expression vector—restriction enzymes must be used again to excise the DNA of interest from the cloning vector, and then DNA ligase is used again to ligate the DNA of interest into the chosen expression vector.

The ability to transfer a DNA of interest to an appropriate expression vector is often limited by the availability or suitability of restriction enzyme recognition sites. Often multiple restriction enzymes must be employed to remove the desired coding region. Further, the reaction conditions used for each enzyme may differ such that it is necessary to perform the excision reaction in separate steps, or it may be necessary to remove a particular enzyme used in an initial restriction enzyme reaction prior to completing subsequent restriction enzyme digestions due to buffer and/or cofactor incompatibility. Many of these extra steps require time-consuming purification of the subcloning intermediate.

There is, therefore, a need to develop protocols and compositions for the rapid transfer of a DNA molecule of interest from one vector to another in vitro or in vivo without the need to rely upon restriction enzyme digestions. To address this need, a number of different sequence specific recombinase based methods have been developed which allow one to transfer sequence material among vectors without restriction enzyme digestions. These systems include the commercially available Creator and Gateway sequence specific recombinase based methods, where representative systems are described in U.S. Pat. Nos. 5,581,808 and 5,888,732; as well as in Published PCT Application Serial Nos. WO 00/12687 and WO 01/05961.

While the above protocols and systems are effective, there is room for improvement. For example, in the above systems, expression vectors that are produced by the methods encode fusion proteins of the gene of interest fused to a sequence encoded by the sequence specific recombinase site of the vector. In many instances, such a fusion sequence is undesirable.

As such, there is continued interest in the improvement of these sequence specific recombinase systems. Of particular interest would be the development of such a system that produced expression vectors where the protein of interest was not expressed a fusion with sequence specific recombinase encoded sequences. The present invention satisfies this interest.

Relevant Literature

References of interest include: U.S. Pat. Nos. 5,527,695; 5,744,336; 5,851,808; 5,888,732; and 5,962,255; as well as in Published PCT Application Serial Nos. WO 00/12687 and WO 01/05961. Also of interest is: Kaartinen & Nagy, Genesis (2001) 31: 126–129; and Yoshimura et al., Mol. Urol. (2001) 5: 81–4.

SUMMARY OF THE INVENTION

Methods are provided for producing a vector that includes at least one splicable intron. In the subject methods, intron containing vectors are produced from donor and acceptor vectors that each include a sequence specific recombinase site, where the subject donor and acceptor vectors further include splice donor and acceptor sites that, upon sequence specific recombination of the donor and acceptor vectors, define an intron in the product vector of the recombination step. Also provided are compositions for use in practicing the subject methods, including the donor and acceptor vectors themselves, as well as systems and kits that include the same. The subject invention finds use in a variety of different applications, including the production of expression vectors that encode C-terminal tagged fusion proteins, the production of expression vectors that encode pure protein and not a fusion thereof with N- and/or C-terminal sequence specific recombinase site encoded residues, and the like.

DEFINITIONS

Figure 1:
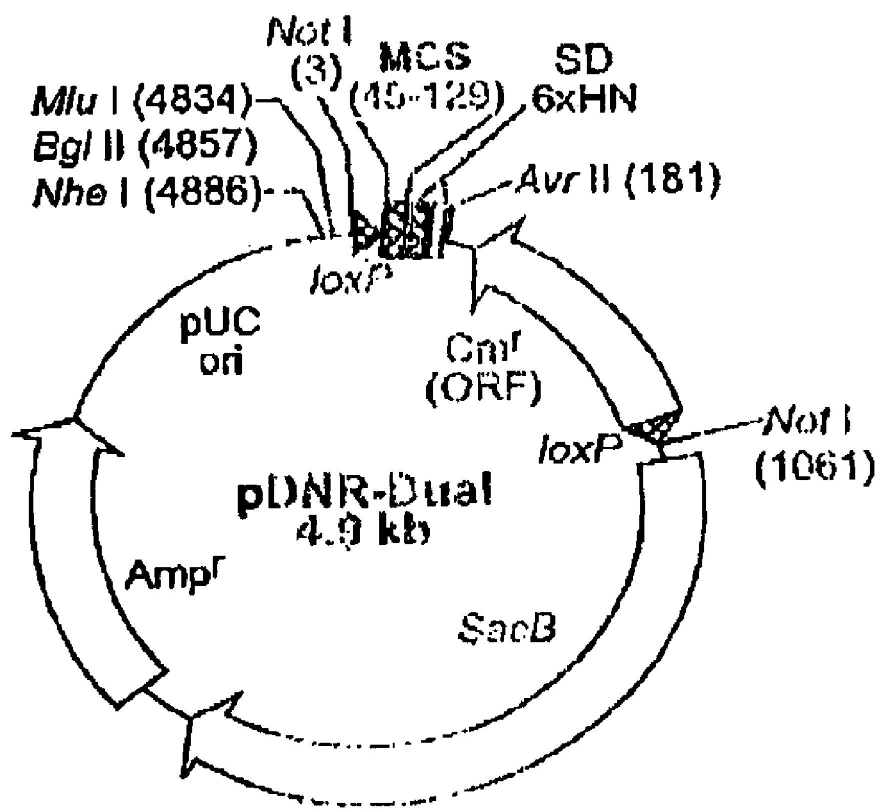
FIG. 1 provides a map of the pDNR-Dual donor vector described in greater detail below.

The terms "sequence-specific recombinase" and "site-specific recombinase" refer to enzymes or recombinases that recognize and bind to a short nucleic acid site or "sequence-specific recombinase target site", i.e., a recombinase recognition site, and catalyze the recombination of nucleic acid in relation to these sites. These enzymes include recombinases, transposases and integrases.

The terms "sequence-specific recombinase target site", "site-specific recombinase target site", "sequence-specific target site" and "site-specific target site" refer to short nucleic acid sites or sequences, i.e., recombinase recognition sites, which are recognized by a sequence- or site-specific recombinase and which become the crossover regions during a site-specific recombination event. Examples of sequence-specific recombinase target sites include, but are not limited to, lox sites, att sites, dif sites and frt sites.

The term "lox site" as used herein refers to a nucleotide sequence at which the product of the cre gene of bacteriophage P1, the Cre recombinase, can catalyze a site-specific recombination event. A variety of lox sites are known in the art, including the naturally occurring loxP, loxB, loxL and loxR, as well as a number of mutant, or variant, lox sites, such as loxP511, loxP514, loxΔ86, loxΔ117, loxC2, loxP2, loxP3 and lox P23.

The term "frt site" as used herein refers to a nucleotide sequence at which the product of the FLP gene of the yeast 2 micron plasmid, FLP recombinase, can catalyze site-specific recombination.

The term "unique restriction enzyme site" indicates that the recognition sequence of a given restriction enzyme appears once within a nucleic acid molecule.

A restriction enzyme site or restriction site is said to be located "adjacent to the 3' end of a sequence-specific recombinase target site" if the restriction enzyme recognition site is located downstream of the 3' end of the sequence-specific recombinase target site. The adjacent restriction enzyme site may, but need not, be contiguous with the last or 3' most nucleotide comprising the sequence-specific recombinase target site.

The term "intron" as used herein refers to a domain of a vector produced by the subject methods that is flanked on the 5' end by a splice donor site and on the 3' end by a splice acceptor site, where under appropriate conditions the intron is spliced out of or removed from an mRNA sequence expressed from the vector in which it is present.

The term "splice donor site" as used herein refers to a sequence or domain of a nucleic acid present at the 5' end of an intron, as defined above, that marks the start of the intron and its boundary with the preceding coding sequence-exon.

The term "splice acceptor site" as used herein refers to a sequence or domain of a nucleic acid present at the 3' end of an intron,as defined above, that marks the start of the intron and its boundary with the following coding sequence-exon. In the present invention, the splice acceptor site is also meant to include the intron Branch point, which is required together with the splice donor and splice acceptor sequence in order for splicing to occur. The branch point marks the point to which the 5' end of the intron becomes joined during the process of splicing. For convenience, in the present embodiments, the splice Acceptor sequence and the Branch site are placed adjacent to each other so that they can be encoded within a single synthetic oligonucleotide for ease of vector construction. Thus, they are described here as a single unit. However, they may be further separated, by moving the branch site further 5' of the splice acceptor sequence, provided that it is not moved 5' of the splice donor sequence and provided that splicing efficiency is not hindered.

The Term "splice site" as used herein refers to a sequence or domain of a nucleic acid present at either the 5' end or the 3' end of an intron as defined above.

The terms "polylinker" or "multiple cloning site" refer to a cluster of restriction enzyme sites, typically unique sites, on a nucleic acid construct that can be utilized for the insertion and/or excision of nucleic acid sequences, such as the coding region of a gene, loxP sites, etc.

The term "termination sequence" refers to a nucleic acid sequence which is recognized by the polymerase of a host cell and results in the termination of transcription. Prokaryotic termination sequences commonly comprise a GC-rich region that has a two-fold symmetry followed by an AT-rich sequence. A commonly used termination sequence is the T7 termination sequence. A variety of termination sequences are known in the art and may be employed in the nucleic acid constructs of the present invention, including the TINT3, TL13, TL2, TR1, TR2, and T6S termination signals derived from the bacteriophage lambda, and termination signals derived from bacterial genes, such as the trp gene of *E. coli.*

The terms "polyadenylation sequence" (also referred to as a "poly $A^+$ site" or "poly $A^+$ sequence") as used herein denotes a DNA sequence which directs both the termination and polyadenylation of the nascent RNA transcript. Efficient polyadenylation of the recombinant transcript is desirable, as transcripts lacking a poly $A^+$ tail are typically unstable and rapidly degraded. The poly $A^+$ signal utilized in an expression vector may be "heterologous" or "endogenous". An endogenous poly $A^+$ signal is one that is found naturally at the 3' end of the coding region of a given gene in the genome. A heterologous poly $A^+$ signal is one which is isolated from one gene and placed 3' of another gene, e.g., coding sequence for a protein. A commonly used heterologous poly $A^+$ signal is the SV40 poly $A^+$ signal. The SV40 poly $A^+$ signal is contained on a 237 bp BamHI/Bc/l restriction fragment and directs both termination and polyadenylation; numerous vectors contain the SV40 poly $A^+$ signal. Another commonly used heterologous poly $A^+$ signal is derived from the bovine growth hormone (BGH) gene; the BGH poly $A^+$ signal is also available on a number of commercially available vectors. The poly $A^+$ signal from the Herpes simplex virus thymidine kinase (HSV tk) gene is also used as a poly $A^+$ signal on a number of commercial expression vectors.

As used herein, the terms "selectable marker" or "selectable marker gene" refer to a gene which encodes an enzymatic activity and confers the ability to grow in medium lacking what would otherwise be an essential nutrient; in addition, a selectable marker may confer upon the cell in which the selectable marker is expressed, resistance to an antibiotic or drug. A selectable marker may be used to confer a particular phenotype upon a host cell. When a host cell must express a selectable marker to grow in selective medium, the marker is said to be a positive selectable marker (e.g., antibiotic resistance genes which confer the ability to grow in the presence of the appropriate antibiotic). Selectable markers can also be used to select against host cells containing a particular gene; selectable markers used in this manner are referred to as negative selectable markers.

As used herein, the term "construct" is used in reference to nucleic acid molecules that transfer DNA segment(s) from one cell to another. The term "vector" is sometimes used interchangeably with "construct". The term "construct" includes circular nucleic acid constructs such as plasmid constructs, phagemid constructs, cosmid vectors, etc., as well as linear nucleic acid constructs including, but not limited to, PCR products. The nucleic acid construct may comprise expression signals such as a promoter and/or an enhancer in operable linkage, and then is generally referred to as an "expression vector" or "expression construct".

The term "expression construct" as used herein refers to an expression module or expression cassette made up of a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter and a ribosome binding site, often along with other sequences. Eukaryotic cells are known to utilize promoters, enhancers, and termination and polyadenylation signals.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The terms also refer to the linkage of amino acid sequences in such a manner so that the reading frame is maintained and a functional protein is produced.

A cell has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations. An organism, such as a plant or animal, that has been transformed with exogenous DNA is termed "transgenic".

Transformation of prokaryotic cells may be accomplished by a variety of means known in the art, including the treatment of host cells with $CaCl_2$ to make competent cells, electroporation, etc. Transfection of eukaryotic cells may be accomplished by a variety of means known in the art, including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

As used herein, the term "host" is meant to include not only prokaryotes, but also eukaryotes, such as yeast, plant and animal cells. A recombinant DNA molecule or gene can be used to transform a host using any of the techniques commonly known to those of ordinary skill in the art. Prokaryotic hosts may include *E. coli, S. tymphimurium, Serratia marcescens* and *Bacillus subtilis.* Eukaryotic hosts include yeasts such as *Saccharomyces cerevisiae, Schizosaccharomyces pombe, Pichia pastoris,* mammalian cells and insect cells, and, plant cells, such as *Arabidopsis thaliana* and *Tobaccum nicotiana.*

As used herein, the terms "restriction endonucleases" and "restriction enzymes" refer to bacterial enzymes, each of which cut double-stranded DNA at or near a specific nucleotide sequence.

"Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing", "molecular cloning" and "genetic engineering". The product of these manipulations results in a "recombinant" or "recombinant molecule". The term "recombinant protein" or "recombinant polypeptide" as used herein refers to a protein molecule that is expressed from a recombinant DNA molecule.

The ribose sugar is a polar molecule, and therefore, DNA is referred to as having a 5' to 3' , or 5' to 3', directionality. DNA is said to have "5' ends" and "3' ends" because mononucleotides are reacted to make oligonucleotides in a manner such that the 5' phosphate of one mononucleotide pentose ring is attached to the 3' oxygen of its neighbor via a phosphodiester linkage. Therefore, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also has a 5' to 3' orientation. In either a linear or circular DNA molecule, discrete elements are referred to as being "upstream" or "5'" of the "downstream" or "3'" elements. This terminology reflects the fact that DNA has an inherent 5' to 3' polarity, and transcription typically proceeds in a 5' to 3' fashion along the DNA strand. The promoter and enhancer elements which direct transcription of an operably linked coding region, or open reading frame, are generally located 5' , or upstream, of the coding region. However, enhancer elements can exert their effect even when located 3' of the promoter and coding region. Transcription termination and polyadenylation signals are typically located 3' or downstream of the coding region.

The 3' end of a promoter is said to be located upstream of the 5' end of a sequence-specific recombinase target site when, moving in a 5' to 3' direction along the nucleic acid molecule, the 3' terminus of a promoter precedes the 5' end of the sequence-specific recombinase target site. When the acceptor construct is intended to permit the expression of a translation fusion, the 3' end of the promoter is located upstream of both the sequences encoding the amino-terminus of a fusion protein and the 5' end of the sequence-specific recombinase target site. Thus, the sequence-specific recombinase target site is located within the coding region of the fusion protein (i.e., located downstream of both the promoter and the sequences encoding the affinity domain, such as Gst).

As used herein, the term "adjacent", in the context of positioning of genetic elements in the constructs, shall mean within about 0 to 2500, sometimes 0 to 1000 bp and sometimes within about 0 to 500, 0 to 400, 0 to 300 or 0 to 200 bp.

A DNA "coding sequence" is a double-stranded DNA sequence that is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence. A "cDNA" is defined as copy-DNA or complementary-DNA, and is a product of a reverse transcription reaction from an mRNA transcript. An "exon" is an expressed sequence transcribed from the gene locus, whereas an "intron" is a non-expressed sequence that is from the gene locus.

Transcriptional and translational control sequences are DNA regulatory sequences, such as promoters, enhancers, polyadenylation signals, terminators, and the like, that provide for the expression of a coding sequence in a host cell. A "cis-element" is a nucleotide sequence, also termed a "consensus sequence" or "motif," that interacts with proteins that can upregulate or downregulate expression of a specific gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes.

A "promoter sequence" is a DNA regulatory region capable of binding RNA polymerase in a cell and initiating transcription of a downstream (3' direction) coding sequence. For purposes of defining the present invention, the promoter sequence includes, at its 3' terminus, the transcription initiation site and extends upstream (in the 5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length.

As used herein, "an origin of replication" or "origin" refers to any sequence capable of directing replication of a DNA construct in a suitable prokaryotic or eukaryotic host (e.g., the ColE1 origin and its derivatives; the yeast 2$\mu$ origin). Eukaryotic expression vectors may also contain "viral replicons" or "origins of replication". Viral replicons are viral DNA sequences which allow for the extrachromosomal replication of a vector in a host cell expressing the appropriate replication factors. Vectors which contain either the SV40 or polyoma virus origin of replication replicate to high copy number (up to $10^4$ copies/cell) in cells that express the appropriate viral T antigen. Vectors which contain the replicons from bovine papillomavirus or Epstein-Barr virus replicate extrachromosomally at low copy number (~100 copies/cell).

As used herein, the terms "nucleic acid molecule encoding", "DNA sequence encoding", and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "gene" means the deoxyribonucleotide sequences comprising the coding region of a structural gene, i.e., the coding sequence for a protein or polypeptide of interest, including sequences located adjacent to the coding region on both the 5' and 3' ends for a distance of about 1 kb on either end, such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences". Introns are segments of a gene that are transcribed into heteronuclear RNA (hnRNA); introns may contain regulatory elements such as enhancers. Introns are removed or "spliced out" from the nuclear or primary transcript; introns therefore are absent in the mature messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

As used herein, the term "purified" or "to purify" refers to the removal of contaminants from a sample. For example, recombinant Cre polypeptides are expressed in bacterial host cells (e.g., as a GST-Cre or $(HN)_6$-Cre fusion protein) and the Cre polypeptides are purified by the removal of host cell proteins; the percent of recombinant Cre polypeptides is thereby enriched or increased in the sample.

As used herein the term "portion" refers to a fraction of a sequence, gene or protein. "Portion" may comprise a fraction greater than half of the sequence, gene or protein, equal to half of the sequence, gene or protein or less than half of the sequence, gene or protein. Typically as used herein, two or more "portions" combine to comprise a whole sequence, gene or protein.

As used herein, the term "fusion protein" refers to a chimeric protein containing a protein of interest joined to an exogenous protein fragment. The fusion partner may enhance solubility of the protein of interest as expressed in a host cell, may provide an affinity tag to allow purification of the recombinant fusion protein from the host cell or culture supernatant, or both. If desired, the fusion protein may be removed from the protein of interest by a variety of enzymatic or chemical means known to the art.

DESCRIPTION OF THE SPECIFIC EMBODIMENTS

Methods are provided for producing a vector that includes at least one splicable intron. In the subject methods, intron containing vectors are produced from donor and acceptor vectors that each include a site specific recombinase site, where the subject donor and acceptor vectors further include splice donor and acceptor sites that, upon site specific recombination of the donor and acceptor vectors, define an intron in the product vector of the recombination step. Also provided are compositions for use in practicing the subject methods, including the donor and acceptor vectors themselves, as well as systems and kits that include the same. The subject invention finds use in a variety of different applications, including the production of expression vectors that encode C-terminal tagged fusion proteins, the production of expression vectors that encode pure protein and not a fusion thereof, and the like.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing various invention components that are described in the publications which might be used in connection with the presently described invention.

In further describing the subject invention, the subject methods are reviewed first in greater detail, followed by a review of representative applications in which the subject methods find use, as well as a review of systems, libraries and kits for use in practicing the subject methods.

Methods

As summarized above, the subject invention provides recombinase-based methods for producing intron containing vectors. In other words, the subject invention provides methods of producing vectors that include at least one intron, where the methods are site specific recombinase based methods. By "site specific recombinase" based method is meant that the subject methods employ a recombinase mechanism to produce the subject intron containing vectors. The recombinase mechasism that is employed in the subject methods is one in which a recombinase mediates the transfer of a nucleic acid from a donor to an acceptor vector, where the donor and acceptor vectors each include at least one recombinase recognition site. A variety of different site specific recombinase systems suitable for transferring a nucleic acid from a donor to an acceptor vector are known and may be modified to be useful in the subject invention. Such systems include those described in U.S. Pat. Nos. 5,851,808; 5,888,732; and U.S. Provisional Application Ser. No. 09/616,651, the disclosure of which are herein incorporated by reference, as well as WO 00/12687 and WO 01/05961, the disclosures of the priority documents of which are herein incorporated by reference.

In general, in addition to each including at least one recombinase recognition site, the donor and acceptor vectors each include at least one splice site, e.g., a splice donor site or a splice acceptor site. In certain embodiments, the donor and acceptor vectors each include a single splice site, where in many of these embodiments, the donor vector includes a splice donor site and the acceptor vector includes a splice acceptor site. In yet other embodiments, the donor and acceptor vectors each include splice donor and acceptor sites which are oriented such that they do not form an intron in the donor vectors but, upon recombinase mediated recombination of the donor and acceptor vectors, produce a resultant vector with two distinct introns. In such designs, the acceptors will contain one synthetic intron that encompasses the recombinase recognition sequence and the acceptor partial selectable marker.

Any convenient splice sites (i.e., splice donor and acceptor sites) may be employed in the vectors of the subject method. Representative splice sites or sequences, e.g., domains, of interest that may be employed include both splice sites that require specifically provided factors for splicing, e.g., eukaryotic host factors (as found in a eukaryotic host cells) such that the intron is only spliced in a eukaryotic host cell or an mimetic (e.g., in vivo or in vitro) environment that provides all the relevant factors, and splice sites that are self-splicing or autocatalytic, i.e., do not require specific factors for splicing to occur, and thus are spliced in both eukaryotic and prokaryotic environments, as well as in vitro environments. Examples include the splicing elements of Group I and Group II self-splicing introns found in bacteria, and certain cellular organelles, e.g., the highly conserved in Group I self-splicing intron, P7; the bacterial group II intron *L. lactis* L1.ltrB; the yeast mitochondrial group II introns aI1 and aI2; and the bacterial group II intron *Sinorhizobium meliloti* RmInt1 (see Oe Y., et al.,2001; and Martinez-Abarca, F. and Toro, N., 2000)

Any convenient splice acceptor donor and acceptor sites may be employed. Consensus sequences for the 5' splice donor site and the 3' splice acceptor site used in RNA splicing are well known in the art (See, Moore, et al., 1993, The RNA World, Cold Spring Harbor Laboratory Press, p. 303–358). In addition, modified consensus sequences that maintain the ability to function as 5' donor splice sites and 3' splice acceptors sites may be used in the practice of the invention. In certain embodiments, splice-donor sites have a characteristic consensus sequence represented as: (A/C) AGGURAGU (where R denotes a purine nucleotide) with the GU in the fourth and fifth positions being required (Jackson, I. J. , Nucleic Acids Research 19: 3715–3798 (1991)). Splice-donor sites are functionally defined by their ability to effect the appropriate reaction within the mRNA splicing pathway. An unpaired splice-donor site is defined herein as a splice-donor site which is present in a donor or acceptor vector, typically a donor vector, and is not accompanied in the vector by a splice-acceptor site positioned 3' to the unpaired splice-donor site. Upon recombinase mediated recombination between the donor and acceptor vectors, the unpaired splice-donor site results in splicing to a splice-acceptor site originally present in the other vector. A splice-acceptor site is a sequence which, like a splice-donor site, directs the splicing of an intron out of a resultant expression cassette produced upon recombinase mediated recombination of the donor and acceptor vectors. Acting in conjunction with a splice-donor site, the splicing apparatus uses a splice-acceptor site to effect the removal of an intron. Splice-acceptor sites have a characteristic sequence represented as: YYYYYYYYYYNYAG, where Y denotes any pyrimidine and N denotes any nucleotide (Jackson, I. J. , Nucleic Acids Research 19:3715–3798 (1991)). For convenience, in the present embodiments, the splice acceptor sequence is immediately preceded by the intron Branch site and these are considered here as one unit, although the may be separated. The consensus Branch site is: YNYYRAY, where Y denotes any pyrimidine, R any purine, and N denotes any nucleotide.

Specific splice sites of interest include, but are not limited to: (a) the novel consensus intron sequences and the Human hemoglobin Beta donor and acceptor sequences described in Liu Z. et al Anal Biochem 246: 264–267 (1997) and found in the experimental section, infra; (b) the donor and acceptor sequences found in the SV40 late 19s and 16s mRNA introns (see pCMV myc from Clontech ); (c) the splice donor and acceptor sequences found in the rabbit Beta globin intron (found in the vector pCMV-neo-Bam); and the like.

The position of the splice donor and acceptor sequences in the various donor and acceptor vectors determines the location of the intron in the resultant product vector and, therefore, the domain that is spliced out of the resultant vector under appropriate splicing conditions, e.g., in a eukaryotic host cell. Thus, by knowing how the acceptor and donor vectors recombine into a resultant vector, one can position the donor and acceptor splice sites in the donor and acceptor vectors to provide for an intron in any location of the resultant vector, and therefore removal of any sequence of the resultant vector. For example, the donor and acceptor splice sites can be positioned to provide for a spliceable intron in the resultant product vector that includes the 3' recombinase recognized site, the 5' recombinase recognized site, etc. See, e.g., the experimental section below for more details with respect to a donor and acceptor vector system in which the donor and acceptor splice sites are positioned to provide for a resultant vector in which the 3' recombinase site (lox) is present in a spliceable intron.

In many embodiments of interest, the donor and acceptor vectors are further characterized in that one of the donor and acceptor vectors includes only one recombinase recognition site, while the other of the donor and acceptor vectors includes two recombinase recognition sites. As mentioned above, in many embodiments, the donor vector includes two recombinase recognition sites while the acceptor vector includes a single recombinase recognition site. In an alternative embodiment, the donor vector includes a single recombinase recognition site while the acceptor vector includes two recombinase recognition sites. Such a system is described in U.S. application Ser. No. 09/616,651, the disclosure of which is herein incorporated by reference.

A feature of the vectors of these embodiments is that the donor and acceptor vectors must be able to recombine in the presence of a suitable recombinase to produce an expression vector as described above, where the expression vector lacks at least a portion of the initial donor or acceptor vector, i.e., it is a non-fusion expression vector. As such, the donor and acceptor vectors must be able to participate in a recombination event that is other than a fusion event, where by fusion event is meant an event in which two complete vectors are fused in their entirety into one fused vector, e.g., where two plasmids are fused together to produce one plasmid that includes all of material from the initial two plasmids, i.e., a fusion plasmid. As such, the subject methods of these particular embodiments are not fusion methods, where such methods are defined as those methods in which a single vector is produced from two or more initial vectors in their entirety, such that all of the initial vector material of each parent vector, e.g., plasmid, is present in its entirety in the resultant fusion vector.

The donor and acceptor vectors of these particular embodiments are further characterized in that one of the donor and acceptor vectors includes only one recombinase recognition site, while the other of the donor and acceptor vectors includes two recombinase recognition sites. In a first preferred embodiment, the donor vector includes two recombinase recognition sites while the acceptor vector includes a single recombinase recognition site. In an alternative embodiment, the donor vector includes a single recombinase recognition site while the acceptor vector includes two recombinase recognition sites. The donor and acceptor vectors of this first, preferred embodiment and this second, alternative embodiment, are described in greater detail below.

The donor and acceptor vectors described generally above may be linear or circular, e.g., plasmids, and in many embodiments of the subject invention are plasmids. Where the donor and acceptor vectors are plasmids, the donor and acceptor vectors typically range in length from about 2 kb to 200 kb, usually from about 2 kb to 40 kb and more usually from about 2 kb to 10 kb.

The donor and acceptor vectors are further characterized in certain embodiments in that all of the recombinase recognition sites on the donor and acceptor vectors must be recognized by the same recombinase and should be able to recombine with each other, but within this parameter they may be the same or different, but in many embodiments are usually the same. Recombinase recognition sites, i.e., sequence-specific recombinase target sites, of interest include: Cre recombinase activity recognized sites, e.g., loxP, loxP2, loxP511, loxP514, loxB, loxC2, loxL, loxR, loxΔ86, loxΔ117; att, dif; frt; and the like. The particular recombinase recognition site is chosen, at least in part, based on the nature of the recombinase to be employed in the subject methods.

The Donor Vector

As mentioned above, in a preferred embodiment of the subject methods, the donor vector includes two recombinase recognition sites while the acceptor vector includes a single recombinase recognition site. In the donor vector of these embodiments, the donor vector includes two recombinase recognition sites, capable of recombining with each other, e.g., site 1A and site 1B, that flank or border a first or donor domain, i.e., desired donor fragment, where this domain is the portion of the vector that becomes part of the expression vector produced by the subject methods. The length of the donor domain may vary, but in many embodiments ranges from 1 kb to 200 kb, usually from about 1 kb to 10 kb. The portion of the donor vector that is not part of this donor domain, i.e., the part that is 5' of site 1A and 3' of site 1B, is referred to herein for clarity as the non-donor domain of the donor vector.

The two recombinase recognition sites of the donor vector are characterized in that they are oriented in the same direction and are capable of recombining with each other. By oriented in the same direction it is meant that they have the same head to tail orientation. Thus, the orientation of site 1A is the same as the orientation of site 1B.

The donor domain flanked by the two recombinase recognition sites, i.e., the portion of the vector 3' of the first recombinase site 1A and 5' of the second recombinase site 1B, includes at least the following components: (a) at least one restriction site and (b) at least a portion of a selectable marker, e.g. a coding sequence, a promoter, or a complete selectable marker made up of a coding sequence and a promoter. The donor domain may include at least one restriction site or a plurality of distinct restriction sites, e.g., as found in a multiple cloning site or polylinker, where by restriction site is meant a stretch of nucleotides that has a sequence that is recognized and cleaved by a restriction endonuclease. Where a plurality of restriction sites are present in the donor domain, the number of distinct or different restriction sites typically ranges from about 2 to 5, usually from about 2to 13.

In many embodiments, there are at least two restriction sites, which may or may not be identical depending on the particular protocol employed to produce the donor plasmid, that flank a nucleic acid which is a coding sequence for a protein of interest, where the protein of interest may or may not be known, e.g., it may be a known coding sequence for a known protein or polypeptide or a coding sequence for an as yet unidentified protein or polypeptide, such as where this nucleic acid of interest is a constituent of a library, as discussed in greater detail below. The length of this nucleic acid of interest nucleic acid may vary greatly, but generally ranges from about 18 bp to 20 kb, usually from about 100 bp to 10 kb and more usually from about 1 kb to 3 kb. At least one restriction site and this nucleic acid of interest nucleic acid, when present, are sufficiently close to the 3' end of the first flanking recombinase site, i.e., recombinase recognition site 1A, such that in the expression vector produced from the donor plasmid, expression of the coding sequence of the nucleic acid of interest is driven by a promoter positioned 5' of this first recombinase site. As such, the distance separating this restriction site/nucleic acid of interest nucleic acid from the recombinase site typically ranges from about 1 bp to 150 bp, usually from about 1 bp to 50 bp.

In a first preferred embodiment, the donor domain also generally includes a portion of a selectable marker. By portion of a selectable marker is meant a sub-part of a selectable marker, e.g. a coding sequence or a promoter, which can be joined with a second subpart to produce a functioning selectable marker that confers some selectable phenotype on the host cell in which the expression vector produced by the subject methods is to be propogated. Examples of subparts of selectable markers are coding sequences and promoters. As such, in many embodiments, the portion of the selectable marker present on the donor domain is a coding sequence of a marker gene or a promoter capable of driving expression of the coding sequence of the marker gene, where in certain preferred embodiments, the coding sequence of a marker gene is the portion of the selectable marker present on the donor domain. Examples of coding sequences of interest include, but are not limited to, the coding sequences from the following marker genes: the chloramphenicol resistance gene, the ampicillin resistance gene, the tetracycline resistance gene, the kanamycin resistance gene, the streptomycin resistance gene and the SacB gene from *B. subtilis* encoding sucrase and conferring sucrose sensitivity; and the like. The promoter portions or sub-parts of this selectable marker are any convenient promoters capable of driving expression of the selectable marker in the expression vector produced by the subject methods, see infra, and in many embodiments are bacterial promoters, where particular promoters of interest include, but are not limited to: the Ampicillin resistance promoter, the inducible lac promoter, the tet-inducible promoter from pProTet ($P_{ItetO-1}$)-available from CLONTECH, T7, T3, and SP6 promoters; and the like. The distance of this sub-part or portion of the selectable marker from the 3' end of the second recombinase recognition site, i.e., site 1B, is sufficient to provide for expression of the marker to occur in the final expression vector, where the other part of selectable marker that is required for efficient expression of the selectable marker is present on the other side, i.e., the 5' side of the adjacent recombinase recognition site. This distance typically ranges from about 1 bp to 2.5 kb, usually from about 1 bp to 500 bp.

The length of the donor domain flanked by the first and second recombinase sites of the donor plasmid, i.e., the length of the desired donor fragment, may vary greatly, so long as the above described components are present on the donor domain. Generally, the length is at least about 100 bp, usually at least about 500 bp and more usually at least about 900 bp, where the length may be as great as 100 kb or greater, but generally does not exceed about 20 kb and usually does not exceed about 10 kb. Typically, the length of the donor domain ranges from about 100 bp to 100 kb, usually from about 500 bp to 20 kb and more usually from about 900 bp to 10 kb.

In addition to the above described components, the donor vector may include a number of additional elements, where desired, that are present on the non-donor domain or non-desired donor fragment of the donor vector. For example, the non-donor domain generally includes an origin of replication. This origin of replication may be any convenient origin of replication or ori site, where a number of ori sites are known in the art, where particular sites of interest include, but are not limited to: ColE1 and its derivatives, pMB1, other origins that function in prokaryotic cells, the yeast 2 micron origin and the like. Also present on this non-donor domain of certain preferred embodiments is a selective marker gene that provides for negative selection of the non-donor domain under particular conditions, e.g., negative selection conditions. This marker is fully functional and therefor is made up of a coding sequence operably linked to an appropriate promoter, i.e., is provided by a functional expression module or cassette. Markers of interest that are capable of providing for this negative selection include, but are not limited to: SacB, providing sensitivity to sucrose; ccdB; and the like.

This non-donor domain of the donor vector may further include one or more additional components or elements that impart additional functionality to the donor vector. For example, the donor vector may be a vector that is specifically designed for use in conjunction with a yeast two hybrid assay protocol, e.g., such that one can determine whether the gene of interest present in the donor domain encodes a product that binds to a second protein prior to transferal of the gene of interest to an expression vector. In such embodiments, the non-donor domain typically includes the following additional elements: yeast origins of replication, e.g., the yeast 2 micron origin; yeast selection markers, e.g., URA3, Leu, and trp selection markers; and peptide fragments of yeast transcription factors that are expressed as translational fusions to the gene encoded within the donor-domain; where yeast two hybrid systems are known to those of skill in the art and described in: Fields, S. and O-K. Song. 1989. A novel genetic system to detect protein-protein interactions. *Nature* 340:245–246; Fields, S. and R. Sternglanz. 1994. The two-hybrid system: an assay for protein-protein interactions. *Trends Genet.* 10: 286–292 and the MATCHMAKER system III user manual, available from CLONTECH.

In other embodiments, the non-donor domain and/or donor domains may contain yet other functional elements that provide specific functions to the donor. For example, Donor vectors can be designed that would also function as prokaryotic expression vectors that express the gene of interest encoded on the donor domain in prokaryotic cells either as a native protein or fused to an affinity or epitope tag. Such vectors may include the following elements in their non-donor or donor domains (e.g., 3' of the multiple cloning site): inducible bacterial promoters, such as the lac promoter or the $P_{ItetO-1}$ promoter; affinity or epitope tags, e.g., GST, 6x(HN), myc-tag, HA-Tag, GFP and its derivatives. Donor vectors designed to function as retroviral vectors would additionally include retroviral LTRs and packaging signals in the non-donor domain. Donor vectors for expression in mammalian cells might also encode affinity or epitope tags, e.g., GST, 6x(HN), myc-tag, HA-Tag, GFP and its derivatives; and mammalian constitive or inducible promoters, e.g., the CMV promoter, the tet-inducible promoter, the TK promoter; viral promoters, e.g., T7, T3, SP6. In a preferred embodiment of this particular embodiment of the subject invention, the donor vector is as follows. The donor-partial selectable marker comprises the open reading frame (ORF) for a selectable marker gene, and is placed between the two donor sequence-specific recombinase target sites, adjacent to the second-donor sequence-specific recombinase target site. In a more preferred embodiment of the donor construct, the open reading frame of the selectable marker is situated such that its 5' to 3' orientation is opposite that of the two donor sequence-specific recombinase target sites.

In another embodiment of the donor construct, the donor construct is a closed circle (e.g., a plasmid or cosmid) comprising, in addition to the two donor sequence-specific recombinase target sites, the unique restriction site or polylinker and the selectable marker gene open reading frame, at least one origin of replication, and at least one donor-functional selectable marker gene. The methods of the present invention should not be limited by the origin of replication selected. For example, origins such as those found in the pUC series of plasmid vectors or of the pBR322 plasmid may be used, as well as others known in the art. Those skilled in the art know that the choice of origin depends on the application for which the donor construct is intended and/or the host strain in which the construct is to be propagated.

A variety of selectable marker genes may be utilized, either for the donor-partial selectable marker or for the donor-functional selectable marker, and such genes may confer either positive- or negative-resistance phenotypes; however, the donor-partial and the donor-functional selectable marker genes should be different from one another. In a preferred embodiment, the selectable markers are selected from the group consisting of the chloramphenicol resistance gene, the ampicillin resistance gene, the tetracycline resistance gene, the kanamycin resistance gene, the streptomycin resistance gene and the sacB gene from *B. subtilis* encoding sucrase and conferring sucrose sensitivity. In a more preferred embodiment, the donor-partial selectable marker is a portion of the gene (e.g., the open reading frame) for chloramphenicol resistance and the donor-functional selectable marker gene is the gene for ampicillin resistance. In another preferred embodiment of the donor construct, the origin of replication and the donor-functional selectable marker gene lie 5' of the first-donor sequence-specific recombinase target site.

In another embodiment of the present invention, there is provided a donor construct with all the above-described features, but additionally having a marker gene different from either the donor-functional selectable marker gene or the donor-partial selectable marker gene, wherein the additional marker gene is positioned 5' of the first sequence-specific recombinase target site such that upon combination with a recombinase, the additional marker gene is located on the undesired second donor fragment. This marker gene provides an additional screen to exclude any products that result in recombinants containing the second donor fragment. The marker gene could be, for example, LacZ. In this case, incorrect recombinants would generate blue colonies on X-Gal plates. Alternatively, a more preferred additional marker would be the sacB gene conferring sucrose sensitivity. In this case, any incorrect clones would be killed when grown on sucrose containing medium. The additional marker provides another screen, thereby enhancing the system by further ensuring that only correct recombination products are obtained following recombination and transformation.

In yet another embodiment of the donor construct, the donor construct further comprises a termination sequence placed 3' of the restriction site or polylinker sequence but 5' of the second-donor sequence-specific recombinase target site. In a most preferred embodiment, the termination sequence is placed 5' of the 3' end of the donor-partial selectable marker (e.g. the ORF of the selectable marker gene in the preferred embodiment which is in the 5' to 3' orientation opposite that of both donor sequence specific recombinase target sites). The present embodiment is not be limited by the termination sequence chosen. In one embodiment, the termination sequence is the Ti termination sequence; however, a variety of termination sequences are known to the art and may be employed in the nucleic acid constructs of the present invention, including the T6S, TINT, TL1, TL2, TR1, and TR2 termination signals derived from the bacteriophage lambda, and termination signals derived from bacterial genes such as the trp gene of *E. coli.*

In another preferred embodiment of the donor construct, the donor construct further comprises a polyadenylation sequence placed 3' of the unique restriction site(s) or polylinker but 5' of the second-donor sequence-specific recombinase target site. In a most preferred embodiment, the polyadenylation sequence is placed 5' of the 3' end of the open reading frame of the selectable marker gene similar to the placement described for the termination sequence supra. The present invention should not be limited by the nature of the polyadenylation sequence chosen. In one embodiment, the polyadenylation sequence is selected from the group consisting of the bovine growth hormone polyadenylation sequence, the simian virus 40 polyadenylation sequence and the Herpes simplex virus thymidine kinase polyadenylation sequence.

Also, in a preferred embodiment, the donor construct further comprises a gene or DNA sequence of interest inserted into the unique restriction enzyme site or polylinker. The present invention should not be limited by the size of the DNA of interest inserted into the unique restriction site or polylinker nor the source of DNA (e.g., genomic libraries, cDNA libraries, etc.).

Thus, in a most preferred embodiment of the donor nucleic acid construct, there is provided, in 5' to 3' order: a) a first-donor sequence-specific recombinase target site; b) a nucleic acid or gene of interest; c) termination and polyadenylation sequences; d) an open reading frame for a selectable marker gene in a 5' to 3' orientation opposite to that of the first-donor sequence-specific recombinase target site; e) a second-donor sequence-specific recombinase target site in the same 5' to 3' orientation as the first donor sequence-specific recombinase target site, wherein the second-donor sequence-specific recombinase target site is able to recombine with said first-donor sequence-specific recombinase target site; f) an origin of replication; and g) a donor-functional selectable marker gene.

In addition to the above features, the donor vector also includes at least one splice site, e.g., a splice donor and/or splice acceptor site. Two representa and non-limiting embodiments are now reviewed. In certain embodiments, the donor vector includes a splice donor site that is positioned to provide for an intron flanking the 3' sequence specific recombinase site in the product vector. In these embodiments, the splice donor site is positioned between the 5' and 3' sequence specific recombinase sites and, more usually, 3' of the multiple cloning site or gene of interest and 5' of the second sequence specific recombinase site. These embodiments find use in producing vectors that express the gene of interest as a C-terminal tagged fusion, as a product that does not include sequence encoded by the 3' sequence specific recombinase site, etc. In certain embodiments, the donor vector also includes a splice acceptor site that is immediately 3' of the 5' sequence specific recombinase site. Since the splice acceptor is 5' of the splice donor sites in the vector, the two splice sites to not make a spliceable intron in the donor vector. However, upon recombination with an appropriate acceptor vector, a product vector in which both the 5' and 3' sequence specific recombinase sites are present in distinct introns can be produced. These embodiments are useful in applications where one wishes to express a protein from the product vector in a manner that is free of any residues encoded by the 5' and 3' sequence specific recombinase sites.

The Acceptor Vector

As mentioned above, in a preferred embodiment of the subject invention, the acceptor vector employed in the subject methods is a vector that includes a single recombinase site. In these embodiments, the single recombinase site is flanked on one side by a promoter and on the other side, in certain preferred embodiments, by a portion of a selectable marker, e.g., a promoter or a coding sequence, where in many preferred embodiments described further below, this portion or sub-part of the selectable marker is a second promoter, e.g., a bacterial promoter. In these embodiments, the single recombinase site is flanked by two oppositely oriented promoters, where one of promoters drives expression of the gene of interest in the expression vector produced by the subject methods and the second promoter drives expression of the coding sequence of the recombinant-functional selectable marker in the expression vector produced by the subject methods. In these embodiments, the first promoter is a promoter that is capable of driving expression of the gene of interest in the expression vector, where representative promoters include, but are not limited to the CMV promoter, the tet-inducible promoter; retroviral LTR promoter/enhancer sequences, the TK promoter, bacterial promoters, e.g. the lac promoter, the $P_{LtetO\text{-}1}$ promoter; the yeast ADH promoter and the like. The distance between the first promoter and the recombinase site is one that allows for expression in the final expression vector, where the distance typically ranges from about 1 bp to 1000 bp, usually from about 10 bp to 500 bp. The second promoter is a promoter that is capable of driving expression of the recombinant-functional selectable marker, and is generally a bacterial promoter. Bacterial promoters of interest include, but are not limited to: the Ampicillin promoter, the lac promoter, the $P_{LtetO\text{-}1}$ promoter, the T7 promoter and the like. The distance between the bacterial promoter and the recombinase site is sufficient to provide for expression of the selectable marker in the expression vector and typically ranges from about 1 bp to 2.5 kb, usually from about 1 bp to 200 bp.

As indicated above, in yet other preferred embodiments the acceptor vector lacks the portion or subpart of the selectable marker. In these embodiments, the acceptor vector may be used with a donor vector that includes a complete positive selectable marker in the desired donor fragment flanked by the two recombinase sites, i.e., the donor vector portion located between the 3' end of the first recombinase site and the 5' end of the second recombinase site. Alternatively, the acceptor vector may be used with a donor vector that only includes a partial selectable positive marker, as described above, where the partial marker is nonetheless functional in the resultant expression vector.

The acceptor vector of the embodiments described above may include a number of additional components or elements which are requisite or desired depending on the nature of the expression vector to be produced from the acceptor vector. In many embodiments of the subject invention, the acceptor vector is an acceptor nucleic acid construct comprising: a) an origin of replication capable of replicating the final desired recombination construct or expression vector; b) an acceptor sequence-specific recombinase target site having a defined 5' to 3' orientation; c) a first promoter adjacent to the 5' end of the acceptor sequence-specific recombinase target site; and d) an acceptor-partial selectable marker, wherein the acceptor-partial selectable marker is capable of recombining with a donor-partial selectable marker from a donor construct (or first donor fragment, once the donor construct is resolved) so creating a recombinant-functional selectable marker in a final desired recombination construct. As in the donor construct, the acceptor construct is not limited by the nature of the sequence-specific recombinase target site employed, and in preferred embodiments the sequence-specific recombinase target site may be selected from the group consisting of loxP, loxP2, loxP511, loxP514, loxB, loxC2, loxL, loxR, loxΔ86, loxΔ117, loxP3, loxP23, att, dif, and frt. The acceptor sequence-specific recombinase target site from the acceptor construct does not have to be identical to those on the donor construct; however, the sequence-specific recombinase target sites on the acceptor and donor constructs must be able to recombine with each other.

In a preferred embodiment, the acceptor-partial selectable marker is a second promoter, wherein the second promoter is oriented such that its 5' to 3' orientation is opposite that of the acceptor sequence-specific recombinase target site and the first promoter, and wherein the 3' end of the second promoter is adjacent to the 3' end of the acceptor sequence-specific recombinase target site.

The acceptor construct is not limited by the nature of the origin of replication employed. A variety of origins of replication are known in the art and may be employed on the acceptor nucleic acid constructs of the present invention. Those skilled in the art know that the choice of origin depends on the application for which the acceptor construct is intended and/or the host strain in which the construct is to be propagated. In the case of the acceptor construct, the origin of replication is chosen appropriately such that both the acceptor construct and the final desired recombination construct will be able to replicate in the given host cell.

The acceptor construct also is not limited by the nature of the promoters employed. Those skilled in the art know that the choice of the promoter depends upon the type of host cell to be employed for expressing a gene(s) under the transcriptional control of the chosen promoter. A wide variety of promoters functional in viruses, prokaryotic cells and eukaryotic cells are known in the art and may be employed in the acceptor nucleic acid constructs of the present invention. In a preferred embodiment of the invention, the donor construct contains a gene or DNA sequences of interest and when the donor construct recombines with the acceptor construct, the first promoter of the acceptor construct is positioned such that it will drive expression of the gene or DNA sequences of interest. Thus, a promoter capable of driving the gene or DNA sequences of interest should be chosen for the first promoter. Further, in a preferred embodiment of the present invention, the acceptor-partial selectable marker is a promoter capable of driving the expression of the donor-partial selectable marker ORF from the donor construct (e.g., the promoter for the ampicillin gene from the plasmid pUC19) or a viral promoter including, but not limited to, the T7, T3, and Sp6 promoters.

In yet another preferred embodiment of the acceptor construct, the acceptor construct additionally includes a DNA sequence encoding a peptide affinity domain or peptide tag sequence, wherein the affinity domain or tag sequence is 3' of the first promoter and 5' of the acceptor sequence-specific recombinase target site, such that the expression of the affinity domain or tag sequence is under control of the first promoter, and such that it is in the same translational frame as the acceptor sequence-specific recombinase target site. The present invention is not limited by the nature of the affinity domain or tag sequence employed; a variety of suitable affinity domains are known in the art, including glutathione-S-transferase, the maltose binding protein, protein A, protein L, polyhistidine tracts, etc.; and tag sequences include, but are not limited to the c-Myc Tag, the HA Tag, the FLAG tag, Green Fluorescent Protein (GFP), etc.

In another preferred embodiment of the acceptor vector construct, the acceptor construct additionally includes a DNA sequence encoding a peptide affinity domain or peptide tag sequence, wherein the affinity domain or tag sequence is 3' of an intron splice acceptor sequence placed in the acceptor vector 3' of the partial selectable marker, such that when this vector is recombined with a donor vector of the invention having an appropriately positioned intron splice donor sequence, an expression cassette is generated having a functional synthetic intron and in which the expression of the affinity domain or tag sequence is under control of the first promoter of the acceptor vector, and such that it is in the same translational frame as a gene of interest placed within the donor vector. The present invention is not limited by the nature of the affinity domain or tag sequence employed; a variety of suitable affinity domains are known in the art, including glutathione-S-transferase, the maltose binding protein, protein A, protein L, polyhistidine tracts, etc.; and tag sequences include, but are not limited to the c-Myc Tag, the HA Tag, the FLAG tag, Green Fluorescent Protein (GFP), etc. Since this tag and the gene of interest are in-frame, following splicing, they will be expressed as a single fusion protein, with the Tag being at the C-terminus of the protein.

In another preferred embodiment of the acceptor construct, the acceptor construct further includes an acceptor-functional selectable marker. The present invention is not limited by the nature of the acceptor-functional selectable marker chosen and the selectable marker gene may result in positive or negative selection. In a preferred embodiment, the acceptor-functional selectable marker gene is selected from the group consisting of the chloramphenicol resistance gene, the ampicillin resistance gene, the tetracycline resistance gene, the kanamycin resistance gene, the streptomycin resistance gene and the sacB gene.

Figure 3:
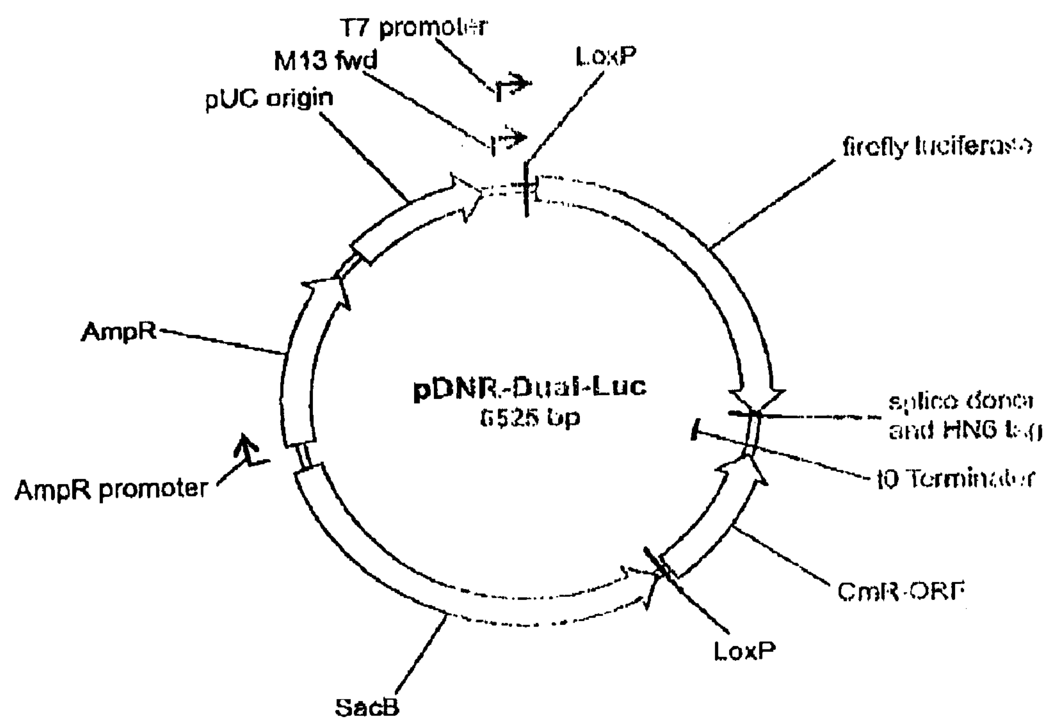
FIG. 3 provides a mape of the pDNR-Dual-Luc vector described in greater detail below.

In addition to one or more of the above described components, the acceptor vectors may include a number of additional components that impart specific function to the expression vectors that are produced from the acceptor vector according to the subject methods. Additional elements that may be present on the subject acceptor vectors include, but are not limited to: (a) elements requisite for generating vectors suitable for use in yeast two hybrid expression assays, e.g., a GAL4 activation domain coding sequence, a GAL4 DNA-binding domain coding sequence, (as found in pLP-GADT7 and pLP-GBKT7 shown in FIGS. 3A & 3B); (b) elements necessary for study of the localization of a protein in a cell, e.g., tagging elements such as fluorescent protein coding sequences, such as the GFP coding sequences; (c) elements necessary for constitutive, bicistronic expression in mammalian cells, e.g., IRES sites, in combination with selectable markers, e.g. antibiotic resistance, fluorescent protein, etc.; (d) elements necessary for inducible expression of the gene of interest on an expression vector, e.g. inducible promoters such as the tet-responsive promoter, etc.; (e) elements that provide for retroviral expression vectors; and the like.

In addition to the above requisite and optional elements, the acceptor vectors further include at least one splice site. Two representative but non-limiting embodiments are now described further. In a first embodiment, the acceptor vector includes a splice acceptor site positioned 3' of the single sequence specific recombinase site of the vector. More precisely, this splice acceptor sequence is placed 3' of the acceptor partial selectable marker sequence. This embodiment finds use in applications where one wishes to produce expression vectors in which the gene of interest is not expressed as a fusion with 3' sequence specific recombinase site encoded domains, etc. In a second respresentative embodiment, the acceptor vector further includes a splice donor site which is positioned 5' of the single sequence specific recombinase site, where this embodiment finds use in those situations where one wishes to produce an expression vector in which the gene of interest is expressed as a protein that does not include either N or C-terminal residues encoded by the 5' and 3' sequence specific recombinase sites.

Product Vector Generation with a Recombinase

As mentioned above, in the subject methods the donor and acceptor vectors are contacted with a recombinase under conditions sufficient for site specific recombination to occur, specifically under conditions sufficient for a recombinase mediated recombination event to occur that produces the desired intron containing product vector, where product vector production is accomplished without cutting or ligation of the donor and acceptor vectors with restriction endonucleases and nucleic acid ligases. The contact may occur under in vitro or in vivo conditions, as is desired and/or convenient.

In many embodiments, an aqueous reaction mixture is produced by combining the donor and acceptor vectors and the recombinase with water and other requisite and/or desired components to produce a reaction mixture that, under appropriate conditions, results in production of the desired expression vector. The various components may be combined separately or simultaneously, depending on the nature of the particular component and how the components are combined. Conveniently, the components of the reaction mixture are combined in a suitable container. The amount of donor and acceptor vectors that are present in the reaction mixture are sufficient to provide for the desired production of the expression vector product, where the amounts of donor and acceptor vector may be the same or different, but are in many embodiments substantially the same if not the same. In many embodiments, the amount of donor and acceptor vector that is present in the reaction mixture ranges from about 50 ng to 2 $\mu$g, usually from about 100 ng to 500 ng and more usually from about 150 ng to 300 ng, for a reaction volume ranging from about 5 $\mu$l to 1000 $\mu$l, usually from about 10 $\mu$l to 50 $\mu$l.

The recombinase that is present in the reaction mixture is one that provides for recombination of the donor and acceptor vectors, i.e. one that recognizes the recombinase recognition sites on the donor and acceptor vectors. As such, the recombinase employed will vary, where representative recombinases include, but are not limited to: recombinases, transposes and integrases, where specific recombinases of interest include, but are not limited to: Cre recombinase (the cre gene has been cloned and expressed in a variety of hosts, and the enzyme can be purified to homogeneity using standard techniques known in the art—purified Cre protein is available commercially from CLONTECH, Novagen, NEB, and others); FLP recombinase of *S. cerevisiae* that recognizes the frt site; Int recombinase of bacteriophage Lambda that recognizes the att site; xerC and xerD recombinases of *E.coli,* which together form a recombinase that recognizes the dif site. the Int protein from the Tn916 transposon; the Tn3 resolvase, the Hin recombinase; the Cin recombinase; the immunoglobulin recombinases; and the like. While the amount of recombinase present in the reaction mixture may vary depending on the particular recombinase employed, in many embodiments the amount ranges from about 0.1 units to 1250 units, usually from about 1 unit to 10 units and more usually from about 1 unit to 2 units, for the above described reaction volumes. The aqueous reaction mixture may include additional components, e.g., a reaction buffer or components thereof, e.g., buffering compounds, such as Tris-HCl; MES; sodium phosphate buffer, sodium acetate buffer; and the like, which are often present in amounts ranging from about 10 mM to 100 mM, usually from about 20 mM to 50 mM; monovalent ions, e.g., sodium, chloride, and the like, which are typically present in amounts ranging from about 10 mM to 500 mM, usually from about 30 mM to 150 mM; divalent cations, e.g., magnesium, calcium and the like, which are often present in amounts ranging from about 1 mM to 20 mM, usually from about 5 mM to 10 mM; and other components, e.g., BSA, EDTA, spermidine and the like; etc (where the above amount ranges are provided for the representative reaction volumes described above). As the reaction mixtures are aqueous reaction mixtures, they also include water.

The subject reaction mixtures are typically prepared at temperatures ranging from about 0–4° C., e.g., on ice, to minimize enzyme activity. Following reaction mixture preparation, the temperature of the reaction mixture is typically raised to a temperature that provides for optimum or maximal recombinase activity, and concomitantly expression vector production. Often, in this portion of the method the temperature will be raised to a temperature ranging from about 4° C. to 37° C., usually from about 10° C. to 25° C., where the mixture will be maintained at this temperature for a period of time sufficient for the desired amount of expression vector production to occur, e.g., for a period of time ranging from about 5 mins to 60 mins, usually from about 10 mins to 15 mins. Following the incubation period, the reaction mixture is subjected to conditions sufficient to inactivate the recombinase, e.g., the temperature of the reaction mixture may be raised to a value ranging from about 65° C. to 70° C. for a period of time ranging from about 5 mins to 10 mins.

Alternatively, contact of the donor and acceptor vectors with the recombinase may occur in vivo, where the donor and acceptor vectors are introduced in a suitable host cell that expresses a recombinase. In this embodiment, the recombination between the donor and acceptor vectors may be accomplished in vivo using a host cell that transiently or constitutively expresses the appropriate site-specific recombinase (e.g., Cre recombinase expressed in the bacterial strain BNN132, available from CLONTECH). pDonor and pAcceptor, i.e., the donor and acceptor vectors respectively, are co-transformed into the host cell using a variety of methods known in the art (e.g., transformation of cells made competent by treatment with $CaCl_2$, electroporation, etc.). The co-transformed host cells are grown under conditions which select for the presence of the recombinant-functional selectable marker created by recombination of pDonor with the pAcceptor (e.g., growth in the presence of chloramphenicol and sucrose when the pDonor vector contains the SacB negative selection marker on the non donor fragment and all or part of the chloramphenicol resistance gene open reading frame and pAcceptor may also contain a promoter necessary for expression of the chloramphenicol open frame). Plasmid DNA is isolated from host cells which grow in the presence of the selective pressure and is subjected to restriction enzyme digestion to confirm that the desired recombination event has occurred.

The present invention also provides a method for the in vitro recombination of nucleic acid constructs, comprising the steps of: a) providing i) a donor nucleic acid construct comprising a donor-partial selectable marker, two donor sequence-specific recombinase target sites each having a defined 5' to 3' orientation and wherein the donor sequence-specific recombinase target sites are placed in the donor construct such that they have the same 5' to 3' orientation, and a unique restriction enzyme site or polylinker, the restriction enzyme site or polylinker being located 3' of the first-donor sequence-specific recombinase target site and 5' of the second-donor sequence-specific recombinase target site; (ii) an acceptor nucleic acid construct comprising an origin of replication, an acceptor sequence-specific recombinase target site having a defined 5' to 3' orientation, a first promoter adjacent to the 5' end of the acceptor sequence-specific recombinase target site, and an acceptor-partial selectable marker, wherein the acceptor-partial selectable marker is capable of recombining with the donor-partial selectable marker from the donor construct to create a recombinant-functional selectable marker in a final desired recombination construct; b) contacting the donor and acceptor constructs in vitro with a site-specific recombinase under conditions such that the desired donor fragment recombines with the acceptor construct to form a final desired recombination construct.

The present invention further provides a method for the recombination of nucleic acid constructs in a host, comprising the steps of: a) providing i) a donor nucleic acid construct comprising a donor-partial selectable marker, two donor sequence-specific recombinase target sites each having a defined 5' to 3' orientation and wherein the donor sequence-specific recombinase target sites are placed in the donor construct such that they have the same 5' to 3' orientation, and a unique restriction enzyme site or polylinker, the restriction enzyme site or polylinker located 3' of the first-donor sequence-specific recombinase target site and 5' of the second-donor sequence-specific recombinase target site; (ii) an acceptor nucleic acid construct comprising an origin of replication, an acceptor sequence-specific recombinase target site having a defined 5' to 3' orientation, a first promoter adjacent to the 5' end of the acceptor sequence-specific recombinase target site, and an acceptor-partial selectable marker, wherein the acceptor-partial selectable marker is capable of recombining with the donor-partial selectable marker from the donor to create a recombinant-functional selectable marker in a final desired recombination construct; and iii) a host cell expressing a site-specific recombinase; b) introducing the donor and acceptor constructs into the host cell under conditions such that the desired donor fragment recombines with the acceptor construct to form the final desired recombination construct which is capable of imparting the ability to the host cell to grow in selective growth medium.

The above methods of producing expression vectors can be employed to rapidly produce a plurality of different expression vectors that are distinct from each other but carry the same coding sequence of interest from a single, original type of donor vector. In other words, the subject methods can be used to rapidly clone a nucleic acid of interest from an initial vector into a plurality of expression vectors. By plurality is meant at least 2, usually at least 5, and more usually at least 10, where the number may be as high as 20, 96 or more. The methods can be performed by one person in a period of time that is a fraction of what it would take by that person of skill in the art to produce the same number and variety of expression vectors using traditional cutting and ligation protocols, where the increase in efficiency obtained by the subject methods is at least about 6 fold, usually at least about 15 fold and more usually at least about 30 fold.

The Resultant Product Vector

The above steps result in the production of an intron containing product vector (i.e. a vector that includes one or more, e.g., one or two, spliceable introns) from donor and acceptor vectors, and in certain embodiments from a portion of one of these vectors and the entirety of the other of these vectors, e.g., from a portion of the donor vector and the entirety of the acceptor vector, where by portion is meant the part of the donor vector that lies 3' of the first donor sequence-specific recombinase site and 5' of the second donor sequence-specific recombinase site. The size of the product vector may vary, depending on the nature of the vector. Where the vector is a plasmid, the size of the expression vector may range from about 3 kb to 20 kb, usually from about 4 kb to 8 kb.

The resultant product vector in many embodiments is characterized in that it includes two recombinase recognition sites, i.e., a first and second recombinase recognition site, oriented in the same direction. The distance between the first and second recombinase sites, specifically the distance between the 3' end of the first recombinase site and the 5' end of the second recombinase site, ranges in many embodiments from about 100 bp to 100 kb, usually from about 500 bp to 20 kb, depending on whether the coding sequence of a protein of interest or just a restriction site/multiple cloning site, is present between the first and second recombinase recognition sites. The portion of the vector that lies in this inter recombinase region, i.e. 3' of the first recombinase site and 5' of the second recombinase site, typically makes up from about 2% to 85%, usually from about 20% to 60% of the entire expression vector.

In many embodiments, the expression vector is further characterized in that 5' of the first recombinase site is a first promoter, 3' of the first recombinase site is at least one restriction site; and the second recombinase site located inside a functional selectable marker, i.e., it is flanked by disparate portions or sub-parts of a selectable marker expression module or cassette (e.g., a promoter and a coding sequence), where the second recombinase site is present between the two sub-parts of the selectable marker in a manner such that the selectable marker is functional, i.e., the coding sequence of the selectable marker is expressed. In other words the expression vector includes a selectable marker expression cassette or module made up of a promoter and coding sequence that flank the second recombinase site. In many embodiments, the second recombinase site is flanked by a promoter on its 3' end and a coding sequence of the selectable marker on its 5' end. In this embodiment, the first and second promoters, located 5' of the first recombinase site and 3' of the second recombinase site, respectively, are oriented in opposite directions.

The expression vector is further characterized by having at least one restriction site, and generally a multiple cloning site, located between the first and second recombinase sites. In many embodiments, located between the first and second recombinase sites, and flanked by two restriction sites, which may or may not be the same, is a nucleic acid of interest, i.e., gene of interest, that includes a coding sequence for a protein of interest whose expression from the expression vector is desired. In these embodiments, the first promoter 5' of the first recombinase site and the coding sequence for the protein of interest are arranged on either side of the first recombinase site such that they form an expression module or cassette that expresses the encoded protein, i.e., the coding sequence and first promoter flank the first recombinase site in manner such that they are operably linked.

In addition to the above features, the expression vector further includes at least one origin of replication that provides for replication in the host or hosts into which it is placed or transformed during use. Origins of replication of interest include, but are not limited to, those described above in connection with the donor and acceptor vectors.

In certain embodiments, the product vector contains a gene or DNA sequence of interest inserted into the unique restriction enzyme site or polylinker such that the gene or DNA sequence of interest is under the control of the first promoter. The gene or DNA sequence of interest is joined to the 3' end of the first-recombinant sequence-specific recombinase target site such that a functional transcriptional unit is formed so that the gene or DNA sequence of interest is expressed as a protein driven by the first promoter of the acceptor construct. In a more preferred embodiment, the gene of interest is joined to the 3' end of the first-recombinant sequence-specific recombinase target site such that a functional translational reading frame is created wherein the gene or DNA sequence of interest is expressed as a fusion protein with an affinity domain or tag sequence derived from the acceptor plasmid and under the expression control of the first promoter of the acceptor construct.

In another preferred embodiment, the gene of interest is joined to the donor splice site such that when the intron is spliced out of the resultant mRNA, the gene of interest is fused in frame to a C-terminal tag derived from the acceptor vector.

In certain embodiments, the product vector further comprises an acceptor-functional selectable marker gene derived from the acceptor construct. If an acceptor-functional selectable marker gene is present in addition to the newly-created recombinant-functional selectable marker, the acceptor-functional selectable marker is a different selectable marker from the newly-created recombinant-functional selectable marker. The present invention should not be limited by the nature of the selectable marker genes chosen; the marker genes may result in positive or negative selection and may be chosen from the group including, but not limited to, the chloramphenicol resistance gene, the ampicillin resistance gene, the tetracycline resistance gene, the kanamycin resistance gene, the streptomycin resistance gene, the strA gene and the sacB gene.

In addition to the above features, the product vector further includes at least one, and typically one to two, spliceable introns. The one or more introns may be positioned anywhere in the product vector. In certain representative embodiments, the 3' recombinase recognized site is present in an intron. In other representative embodiments, the 5' recombinase recognized site is present in an intron. In yet other representative embodiments, both the 5' and 3' recombinase recognized sites are present in introns.

Utility

The subject methods find use in a variety of different applications, where such applications are generally those protocols and methods in which the transfer of a nucleic acid of interest from one vector to another, e.g., the cloning of a nucleic acid from an initial vector into a final vector, is desired. As such, the subject methods are particularly suited for use in cloning nucleic acids of interest, including whole libraries, from an initial vector into an expression vector, where the product vector may be functionalized to express the polypeptide or protein encoded by the nucleic acid of interest located on it in a variety of different desired environments and/or under desired conditions, e.g., in a cell of interest, in response to a particular stimulus, tagged by a detectable marker, etc.

As such, the product vectors produced by the subject methods find use in a variety of different applications, including the study of polypeptide and protein function and behavior, i.e., in the characterization of a polypeptide or protein, either known or unknown; and the like. In the broadest sense, the subject methods find application in any method where traditional digestion and ligation protocols are employed to transfer or clone a nucleic acid from one vector to another, e.g., cloning digestion and ligation protocols, where the expression vectors produced by the subject methods find use in research applications, as well as other applications, e.g., protein production applications, therapeutic applications, and the like.

Depending on the location of the one or more introns in the product vectors, the product vectors find use in the expression of non-fusion proteins, e.g., proteins free of residues at their N- and C-termini that are encoded by sequence specific recombinase sites; N-and or C-termini tagged proteins, etc.

Systems

Also provided are systems for use in practicing the subject methods. The subject systems at least include a donor vector and an acceptor vector as described above. In addition, the subject systems may include a recombinase which recognizes the recombinase sites present on the donor and acceptor vectors. The systems may also include, where desired, a host cell, e.g., in in vivo methods of expression vector production, as described above. Other components of the subject systems include, but are not limited to: reaction buffer, controls, etc.

Libraries

Also provided are nucleic acid libraries cloned into donor and/or acceptor vectors of the subject invention. These nucleic acid libraries are made up of a plurality of individual donor/acceptor vectors where each distinct constituent member of the library has a different nucleic acid portion or component, e.g., genomic fragment, cDNA, of an original whole nucleic acid library, i.e., fragmented genome, cDNA collection generated from the total or partial mRNA of an mRNA sample, etc. In other words, the libraries of the subject invention are nucleic acid libraries cloned into donor or acceptor vectors according to the subject invention, where the nucleic acid libraries include, but are not limited to, genomic libraries, cDNA libraries, etc. Specific donor/acceptor libraries of interest include, but are not limited to: Human Brain Poly A+ RNA; Human Heart Poly A+ RNA; Human Kidney Poly A+ RNA; Human Liver Poly A+ RNA; Human Lung Poly A+ RNA; Human Pancreas Poly A+ RNA; Human Placenta Poly A+ RNA; Human Skeletal Muscle Poly A+ RNA; Human Testis Poly A+ RNA; Human Prostate Poly A+ RNA and the like. With donor libraries according to the subject invention, the subject methods permit the rapid exchange of either individual clones of interest, groups of clones or potentially an entire cDNA library to a variety of expression vectors.

Kits

Also provided are kits for use in practicing the subject methods. The subject kits at least include at least one donor vector and a recombinase that recognizes the recombinase sites of the donor vector. The subject kits may further include other components that find use in the subject methods, e.g., acceptor vectors; reaction buffers, positive controls, negative controls, etc.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

Experimental

EXAMPLE 1

Representative Protocols

A.

Figure 5:
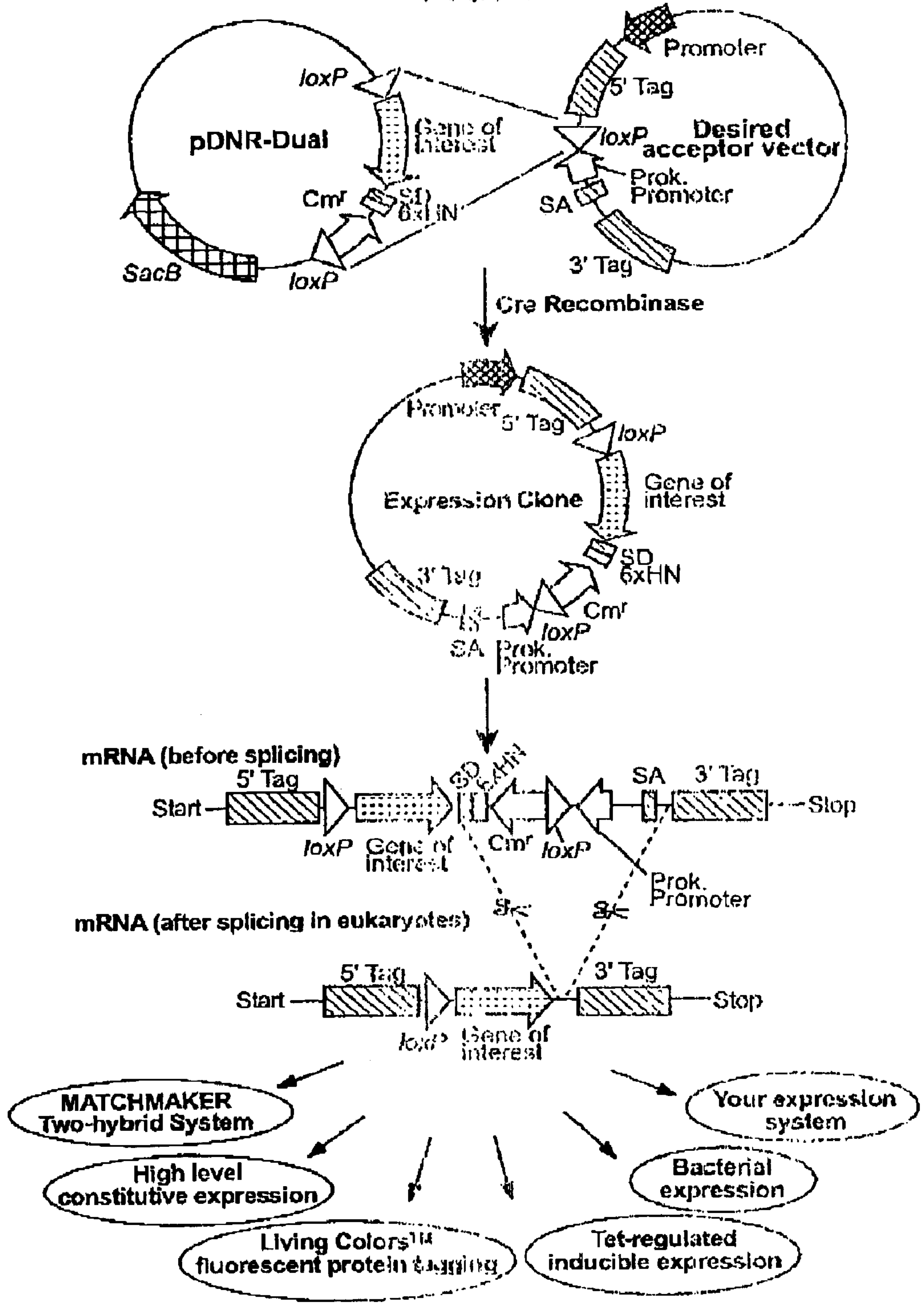
FIG. 5 provides a flow diagram of a representative method according to the subject invention.

FIG. 5 provides a flow diagram of a representative recombinase based method according to the subject invention.

B.

Figure 2:
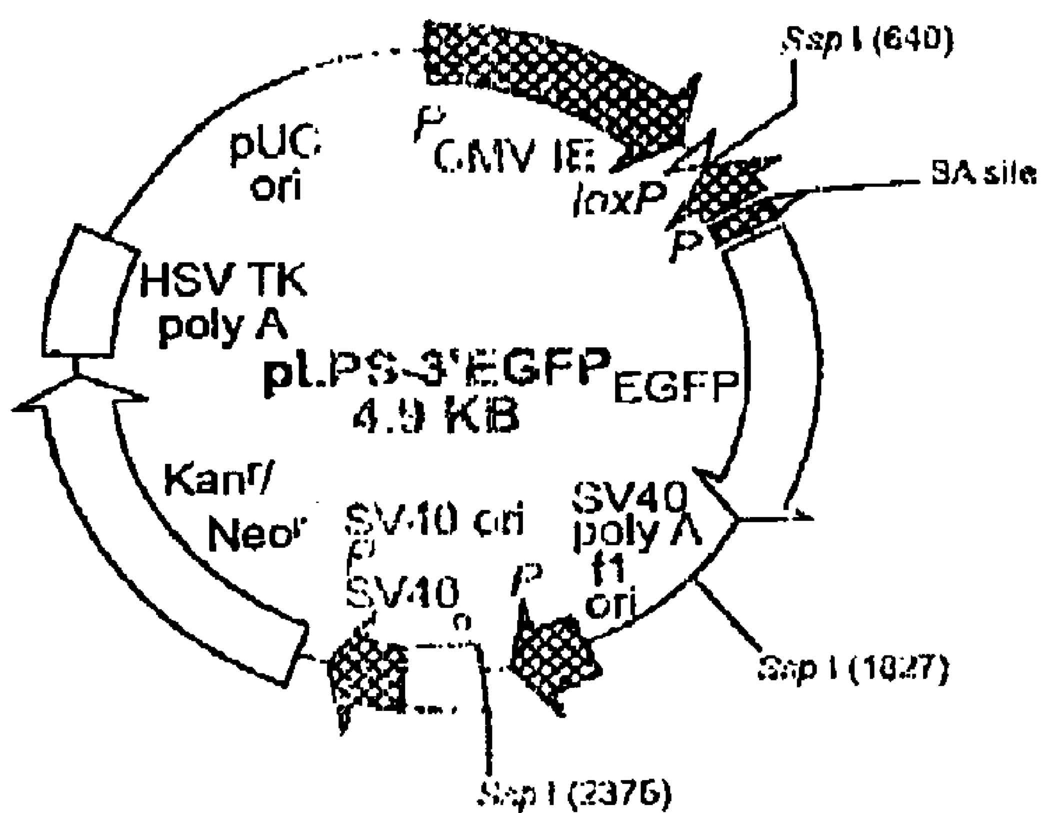
FIG. 2 provides a map of the pLPS-EGFP acceptor vector described in greater detail below.

In order to test the utility of intron-splicing to enable tagging of a protein of interest in a donor vector with a peptide tag or protein in an acceptor vector, a Donor and Acceptor vector capable of splicing were built using standard molecular biology techniques. The Donor vector was called pDNR-Dual. A map of this vector is provided in FIG. 1 and its sequence is provided below as SEQ ID NO:01. The Acceptor vector was called pLPS-EGFP. A map of this vector is provided in FIG. 2 and its sequence is provided below as SEQ ID NO:02. Further, a luciferase test gene was cloned, using standard techniques into the MCS of pDNR-Dual at the SalI and Apa I sites, so as to generate pDNR-Dual-Luc. A map of this vector is provided in FIG. 3 and the sequence of this vector is provided below as SEQ ID NO:03. In so doing, the Luciferase gene was placed such that it had no stop codon and such that it would be in-frame with the EGFP tag present in pLPS-EGFP following Cre/Lox-based transfer from the Donor to the Acceptor.

Figure 4:
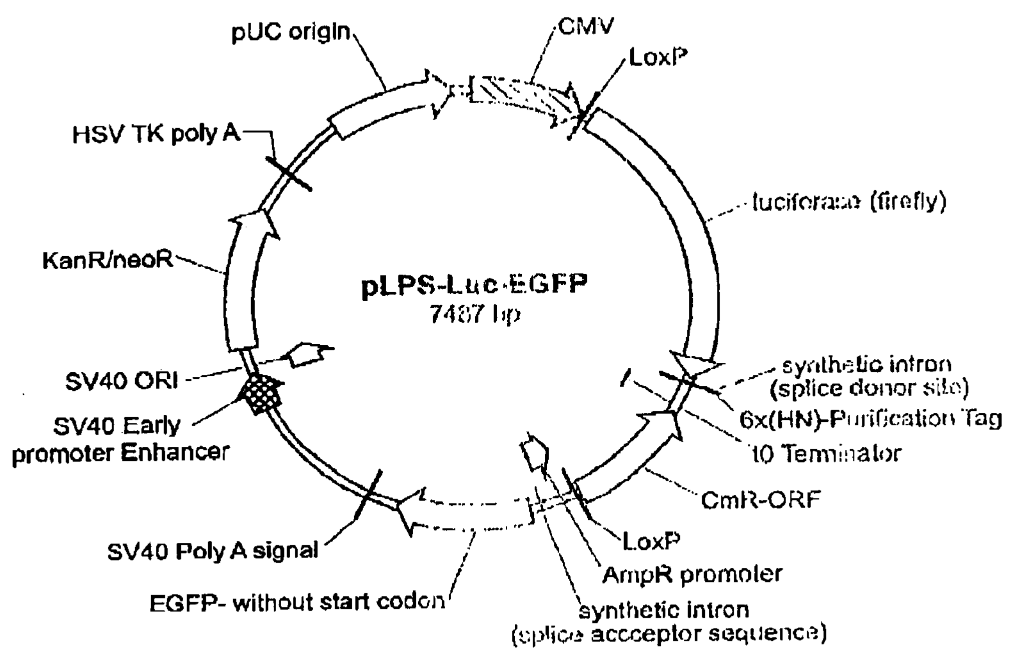
FIG. 4 provides a map of the pLPS-Luc-EGFP vector described in greater detail below.

The pDNR-Dual-Luc and pLPS-EGFP vectors were then recombined in vitro using Cre according to methods described in Clontech's Creator User Manual (Clontech Laboratories Inc., Palo Alto Calif.) (see also the methods disclosed in U.S. application Ser. No. 09/616,651, the disclosure of which is herein incorporated by reference), and an aliquot of the reaction was transformed in to competent *E. coli*. Following selection on chloramphenicol and sucrose plates, recombinant clones were isolated and confirmed by standard restriction mapping and sequencing to encode the expectedrecombinant molecule, having the luciferase gene from the donor vector transferred to the acceptor vector. This vector is called pLPS-Luc-EGFP. A map of this vector is provide in FIG. 4 and the sequence of this vector is provided below as SEQ ID NO:04. This construct thus has both a splice donor sequence, provided from the donor vector, and a splice acceptor sequence, provided by the acceptor vector. Together, these create an artificial intron between the 3' end of the luciferase gene and the 5' end of the EGFP Tag. This intron being composed of the chloramphenicol open reading frame, the second LoxP site, and the ampicillin promoter sequence.

To test if this construct would generate a properly spliced mRNA, so enabling expression of a luciferase EGFP fusion protein, the pLPS-Luc-EGFP vector was then transfected into HEK293 cells using standard procedures known to the art. For comparison, the HEK293 cells were also transfected with a pLuc-EGFP construct. This construct was made by cloning the luciferase gene (without stop codon) in-frame with EGFP into the pEGFP-N1 vector (available from Clontech Laboraries, Inc. Palo Alto Calif.) using standard molecular biology techniques.

Twenty-four hours after transfection, the cells were examined for EGFP fluorescence using a fluorescence microscope. Both the splicing construct (pLPS-Luc-EGFP) and the direct luciferase-EGFP fusion (pLuc-EGFP) showed equivalent EGFP expression over untransfected control cells.

Extracts of the cells were then made and analyzed by western blotting using an anti-luciferase antibody. Again, both the splicing construct (pLPS-Luc-EGFP) and the direct luciferase-EGFP fusion (pLuc-EGFP) showed equivalent expression of the luciferase-EGFP fusion protein. A further analysis of total RNA extracted from cells transfected with the splicing construct (pLPS-Luc-EGFP) by Northern blotting, demonstrated that the mRNA generated from the construct was being efficiently spliced to remove the chloramphenicol sequences.

EXAMPLE 2.

Vector Sequence Information

```
A. pDNR-dual
   1 gcggccgcat aacttcgtat agcatacatt atacgaagtt atcagtcgac ggtaccggac  (SEQ ID NO:01)
  61 atatgcccgg gaattcctgc aggatccgct cgagaagctt tctagaccat tcgtttggcg
 121 cgcgggccca ggtgagtggt cataatcata atcataatca taatcataat cacaactagc
 181 ctaggagatc ctggtcatga ctagtgcttg gattctcacc aataaaaaac gcccggcggc
 241 aaccgagcgt tctgaacaaa tccagatgga gttctgaggt cattactgga tctatcaaca
 301 ggagtccaag cgagctcgat atcaaattac gccccgccct gccactcatc gcagtactgt
 361 tgtaattcat taagcattct gccgacatgg aagccatcac aaacggcatg atgaacctga
 421 atcgcaagcg gcatcagcac cttgtcgcct tgcgtataat atttgcccat ggtgaaaacg
 481 ggggcgaaga agttgtccat attggccacg tttaaatcaa aactggtgaa actcacccag
 541 ggattggctg agacgaaaaa catattctca ataaaccctt tagggaaata ggccaggttt
 601 tcaccgtaac acgccacatc ttgcgaatat atgtgtagaa actgccggaa atcgtcgtgg
 661 tattcactcc agagcgatga aaacgtttca gtttgctcat ggaaaacggt gtaacaaggg
 721 tgaacactat cccatatcac cagctcaccg tctttcattg ccatacgaaa ttccggatga
 781 gcattcatca ggcgggcaag aatgtgaata aaggccggat aaaacttgtg cttatttttc
 841 tttacggtct ttaaaaaggc cgtaatatcc agctgaacgg tctggttata ggtacattga
 901 gcaactgact gaaatgcctc aaaatgttct ttacgatgcc attgggatat atcaacggtg
 961 gtatatccag tgattttttt ctccatttta gcttccttag ctcctgaaag atccataact
1021 tcgtatagca tacattatac gaagttatgc ggccgcgacg tccacatata cctgccgttc
1081 actattattt agtgaaatga gatattatga tattttctga attgtgatta aaaaggcaac
1141 tttatgccca tgcaacagaa actataaaaa atacagagaa tgaaaagaaa cagatagatt
1201 ttttagttct ttaggcccgt agtctgcaaa tccttttatg attttctatc aaacaaaaga
1261 ggaaaataga ccagttgcaa tccaaacgag agtctaatag aatgaggtcg aaaagtaaat
1321 cgcgcgggtt tgttactgat aaagcaggca agacctaaaa tgtgtaaagg gcaaagtgta
1381 tactttggcg tcacccctta catattttag gtcttttttt attgtgcgta actaacttgc
1441 catcttcaaa caggagggct ggaagaagca gaccgctaac acagtacata aaaaaggaga
1501 catgaacgat gaacatcaaa aagtttgcaa aacaagcaac agtattaacc tttactaccg
1561 cactgctggc aggaggcgca actcaagcgt ttgcgaaaga aacgaaccaa aagccatata
1621 aggaaacata cggcatttcc catattacac gccatgatat gctgcaaatc cctgaacagc
1681 aaaaaaatga aaaatatcaa gttcctgagt tcgattcgtc cacaattaaa aatatctctt
1741 ctgcaaaagg cctggacgtt tgggacagct ggccattaca aaacgctgac ggcactgtcg
1801 caaactatca cggctaccac atcgtctttg cattagccgg agatcctaaa aatgcggatg
1861 acacatcgat ttacatgttc tatcaaaaag tcggcgaaac ttctattgac agctggaaaa
1921 acgctggccg cgtctttaaa gacagcgaca aattcgatgc aaatgattct atcctaaaag
1981 accaaacaca agaatggtca ggttcagcca catttacatc tgacggaaaa atccgtttat
2041 tctacactga tttctccggt aaacattacg gcaaacaaac actgacaact gcacaagtta
2101 acgtatcagc atcagacagc tctttgaaca tcaacggtgt agaggattat aaatcaatct
2161 ttgacggtga cggaaaaacg tatcaaaatg tacagcagtt catcgatgaa ggcaactaca
2221 gctcaggcga caaccatacg ctgagagatc ctcactacgt agaagataaa ggccacaaat
2281 acttagtatt tgaagcaaac actggaactg aagatggcta ccaaggcgaa gaatctttat
2341 ttaacaaagc atactatggc aaaagcacat cattcttccg tcaagaaagt caaaaacttc
2401 tgcaaagcga taaaaaacgc acggctgagt tagcaaacgg cgctctcggt atgattgagc
2461 taaacgatga ttacacactg aaaaaagtga tgaaaccgct gattgcatct aacacagtaa
2521 cagatgaaat tgaacgcgcg aacgtcttta aaatgaacgg caaatggtac ctgttcactg
2581 actcccgcgg atcaaaaatg acgattgacg gcattacgtc taacgatatt tacatgcttg
2641 gttatgtttc taattcttta actggcccat acaagccgct gaacaaaact ggccttgtgt
2701 taaaaatgga tcttgatcct aacgatgtaa cctttactta ctcacacttc gctgtacctc
2761 aagcgaaagg aaacaatgtc gtgattacaa gctatatgac aaacagagga ttctacgcag
2821 acaaacaatc aacgtttgcg cctagcttcc tgctgaacat caaaggcaag aaaacatctg
2881 ttgtcaaaga cagcatcctt gaacaaggac aattaacagt taacaaataa aaacgcaaaa
2941 gaaaatgccg atatcctatt ggcattgacg tcaggtggca cttttcgggg aaatgtgcgc
3001 ggaaccccta tttgtttatt tttctaaata cattcaaata tgtatccgct catgagacaa
3061 taaccctgat aaatgcttca ataatattga aaaaggaaga gtatgagtat tcaacatttc
3121 cgtgtcgccc ttattccctt ttttgcggca ttttgccttc ctgtttttgc tcacccagaa
3181 acgctggtga aagtaaaaga tgctgaagat cagttgggtg cacgagtggg ttacatcgaa
```

-continued

```
3241 ctggatctca acagcggtaa gatccttgag agttttcgcc ccgaagaacg ttttccaatg
3301 atgagcactt ttaaagttct gctatgtggc gcggtattat cccgtattga cgccgggcaa
3361 gagcaactcg gtcgccgcat acactattct cagaatgact tggttgagta ctcaccagtc
3421 acagaaaagc atcttaagga tggcatgaca gtaagagaat tatgcagtgc tgccataacc
3481 atgagtgata acactgcggc caacttactt ctgacaacga tcggaggacc gaaggagcta
3541 accgcttttt tgcacaacat gggggatcat gtaactcgcc ttgatagttg ggaaccggag
3601 ctgaatgaag ccataccaaa cgacgagcgt gacaccacga tgcctgtagc aatggcaaca
3661 acgttgcgca aactattaac tggcgaacta cttactctag cttcccggca acaattaata
3721 gactggatgg aggcggataa agttgcagga ccacttctgc gctcggccct tccggctggc
3781 tggtttattg ctgataaatc tggagccggt gagcgtgggt ctcgcggtat cattgcagca
3841 ctggggccag atggtaagcc ctcccgtatc gtagttatct acacgacggg gagtcaggca
3901 actatggatg aacgaaatag acagatcgct gagataggtg cctcactgat taagcattgg
3961 taactgtcag accaagttta ctcatatata ctttagattg atttaaaact tcatttttaa
4021 tttaaaagga tctaggtgaa gatccttttt gataatctca tgaccaaaat cccttaacgt
4081 gagttttcgt tccactgagc gtcagacccc gtagaaaaga tcaaaggatc ttcttgagat
4141 cctttttttc tgcgcgtaat ctgctgcttg caaacaaaaa aaccaccgct accagcggtg
4201 gtttgtttgc cggatcaaga gctaccaact ctttttccga aggtaactgg cttcagcaga
4261 gcgcagatac caaatactgt tcttctagtg tagccgtagt taggccacca cttcaagaac
4321 tctgtagcac cgcctacata cctcgctctg ctaatcctgt taccagtggc tgctgccagt
4381 ggcgataagt cgtgtcttac cgggttggac tcaagacgat agttaccgga taaggcgcag
4441 cggtcgggct gaacgggggg ttcgtgcaca cagcccagct tggagcgaac gacctacacc
4501 gaactgagat acctacagcg tgagctatga gaaagcgcca cgcttcccga agggagaaag
4561 gcggacaggt atccggtaag cggcagggtc ggaacaggag agcgcacgag ggagcttcca
4621 gggggaaacg cctggtatct ttatagtcct gtcgggtttc gccacctctg acttgagcgt
4681 cgatttttyt gatgctcgtc aggggggcgg agcctatgga aaaacgccag caacgcggcc
4741 tttttacggt tcctggcctt ttgctggcct tttgctcaca tgttctttcc tgcgttatcc
4801 cctgattctg tggataaccg tattaccgcc ttacgcgtgt aaaacgacgg ccagtagatc
4861 tgtaatacga ctcactatag ggcgctagct gctcgccgca gccgaacgac cgagcgcagc
4921 gagtcagtga gcgaggaa
```

B. pLPS-EGFP

```
   1 tagttattaa tagtaatcaa ttacggggtc attagttcat agcccatata tggagttccg  (SEQ ID NO:02)
  61 cgttacataa cttacggtaa atggcccgcc tggctgaccg cccaacgacc cccgcccatt
 121 gacgtcaata atgacgtatg ttcccatagt aacgccaata gggactttcc attgacgtca
 181 atgggtggag tatttacggt aaactgccca cttggcagta catcaagtgt atcatatgcc
 241 aagtacgccc cctattgacg tcaatgacgg taaatggccc gcctggcatt atgcccagta
 301 catgacctta tgggactttc ctacttggca gtacatctac gtattagtca tcgctattac
 361 catggtgatg cggttttggc agtacatcaa tgggcgtgga tagcggtttg actcacgggg
 421 atttccaagt ctccacccca ttgacgtcaa tgggagtttg ttttggcacc aaaatcaacg
 481 ggactttcca aaatgtcgta acaactccgc cccattgacg caaatgggcg gtaggcgtgt
 541 acggtgggag gtctatataa gcagagctgg tttagtgaac cgtcagatcc gctagcataa
 601 cttcgtatag catacattat acgaagttat agatccaata ttattgaagc atttatcagg
 661 gttattgtct catgagcgga tacatatttg aatgtattta gaaaaataaa caaatagggg
 721 ttccgcgcac atttccccga aaagtgccac ctgacgtgga tctcgagctc aagcttcgaa
 781 ttcagggttt ccttgacaat atcatactta tcctgtccct ttttttttcca cagctaccgg
 841 tcgcgagcaa gggcgaggag ctgttcaccg gggtggtgcc catcctggtc gagctggacg
 901 gcgacgtaaa cggccacaag ttcagcgtgt ccggcgaggg cgagggcgat gccacctacg
 961 gcaagctgac cctgaagttc atctgcacca ccggcaagct gcccgtgccc tggcccaccc
1021 tcgtgaccac cctgacctac ggcgtgcagt gcttcagccg ctaccccgac cacatgaagc
1081 agcacgactt cttcaagtcc gccatgcccg aaggctacgt ccaggagcgc accatcttct
1141 tcaaggacga cggcaactac aagacccgcg ccgaggtgaa gttcgagggc gacaccctgg
1201 tgaaccgcat cgagctgaag ggcatcgact tcaaggagga cggcaacatc ctggggcaca
1261 agctggagta caactacaac agccacaacg tctatatcat ggccgacaag cagaagaacg
1321 gcatcaaggt gaacttcaag atccgccaca acatcgagga cggcagcgtg cagctcgccg
1381 accactacca gcagaacacc cccatcggcg acggccccgt gctgctgccc gacaaccact
1441 acctgagcac ccagtccgcc ctgagcaaag accccaacga gaagcgcgat cacatggtcc
1501 tgctggagtt cgtgaccgcc gccgggatca ctctcggcat ggacgagctg tacaagtaaa
1561 gcggccgcga ctctagatca taatcagcca taccacattt gtagaggttt tacttgcttt
1621 aaaaaacctc ccacacctcc ccctgaacct gaaacataaa atgaatgcaa ttgttgttgt
1681 taacttgttt attgcagctt ataatggtta caaataaagc aatagcatca caaatttcac
1741 aaataaagca tttttttcac tgcattctag ttgtggtttg tccaaactca tcaatgtatc
1801 ttaaggcgta aattgtaagc gttaatattt tgttaaaatt cgcgttaaat ttttgttaaa
1861 tcagctcatt ttttaaccaa taggccgaaa tcggcaaaat cccttataaa tcaaaagaat
1921 agaccgagat agggttgagt gttgttccag tttggaacaa gagtccacta ttaaagaacg
1981 tggactccaa cgtcaaaggg cgaaaaaccg tctatcaggg cgatggccca ctacgtgaac
2041 catcacccta atcaagtttt ttggggtcga ggtgccgtaa agcactaaat cggaacccta
2101 aagggagccc ccgatttaga gcttgacggg gaaagccggc gaacgtggcg agaaaggaag
2161 ggaagaaagc gaaaggagcg ggcgctaggg cgctggcaag tgtagcggtc acgctgcgcg
2221 taaccaccac acccgccgcg cttaatgcgc cgctacaggg cgcgtcaggt ggcacttttc
2281 ggggaaatgt gcgcggaacc cctatttgtt tatttttcta aatacattca aatatgtatc
2341 cgctcatgag acaataaccc tgataaatgc ttcaataata ttgaaaaagg aagagtcctg
2401 aggcggaaag aaccagctgt ggaatgtgtg tcagttaggg tgtggaaagt ccccaggctc
2461 cccagcaggc agaagtatgc aaagcatgca tctcaattag tcagcaacca ggtgtggaaa
2521 gtccccaggc tccccagcag gcagaagtat gcaaagcatg catctcaatt agtcagcaac
2581 catagtcccg cccctaactc cgcccatccc gcccctaact ccgcccagtt ccgcccattc
2641 tccgccccat ggctgactaa ttttttttat ttatgcagag gccgaggccg cctcggcctc
2701 tgagctattc cagaagtagt gaggaggctt ttttggaggc ctaggctttt gcaaagatcg
2761 atcaagagac aggatgagga tcgtttcgca tgattgaaca agatggattg cacgcaggtt
2821 ctccggccgc ttgggtggag aggctattcg gctatgactg ggcacaacag acaatcggct
2881 gctctgatgc cgccgtgttc cggctgtcag cgcaggggcg cccggttctt tttgtcaaga
```

-continued 2941 ccgacctgtc cggtgccctg aatgaactgc aagacgaggc agcgcggcta tcgtggctgg
3001 ccacgacggg cgttccttgc gcagctgtgc tcgacgttgt cactgaagcg ggaagggact
3061 ggctgctatt gggcgaagtg ccggggcagg atctcctgtc atctcacctt gctcctgccg
3121 agaaagtatc catcatggct gatgcaatgc ggcggctgca tacgcttgat ccggctacct
3181 gcccattcga ccaccaagcg aaacatcgca tcgagcgagc acgtactcgg atggaagccg
3241 gtcttgtcga tcaggatgat ctggacgaag agcatcaggg gctcgcgcca gccgaactgt
3301 tcgccaggct caaggcgagc atgcccgacg gcgaggatct cgtcgtgacc catggcgatg
3361 cctgcttgcc gaatatcatg gtggaaaatg gccgcttttc tggattcatc gactgtggcc
3421 ggctgggtgt ggcggaccgc tatcaggaca tagcgttggc tacccgtgat attgctgaag
3481 agcttggcgg cgaatgggct gaccgcttcc tcgtgcttta cggtatcgcc gctcccgatt
3541 cgcagcgcat cgccttctat cgccttcttg acgagttctt ctgagcggga ctctggggtt
3601 cgaaatgacc gaccaagcga cgcccaacct gccatcacga gatttcgatt ccaccgccgc
3661 cttctatgaa aggttgggct tcggaatcgt tttccgggac gccggctgga tgatcctcca
3721 gcgcggggat ctcatgctgg agttcttcgc ccaccctagg gggaggctaa ctgaaacacg
3781 gaaggagaca ataccggaag gaacccgcgc tatgacggca ataaaaagac agaataaaac
3841 gcacggtgtt gggtcgtttg ttcataaacg cggggttcgg tcccagggct ggcactctgt
3901 cgataccccca ccgagacccc attggggcca atacgcccgc gtttcttcct tttccccacc
3961 ccacccccca agttcgggtg aaggcccagg gctcgcagcc aacgtcgggg cggcaggccc
4021 tgccatagcc tcaggttact catatatact ttagattgat ttaaaacttc atttttaatt
4081 taaaaggatc taggtgaaga tcctttttga taatctcatg accaaaatcc cttaacgtga
4141 gttttcgttc cactgagcgt cagaccccgt agaaaagatc aaaggatctt cttgagatcc
4201 tttttttctg cgcgtaatct gctgcttgca aacaaaaaaa ccaccgctac cagcggtggt
4261 ttgtttgccg gatcaagagc taccaactct ttttccgaag gtaactggct tcagcagagc
4321 gcagatacca aatactgtcc ttctagtgta gccgtagtta ggccaccact tcaagaactc
4381 tgtagcaccg cctacatacc tcgctctgct aatcctgtta ccagtggctg ctgccagtgg
4441 cgataagtcg tgtcttaccg ggttggactc aagacgatag ttaccggata aggcgcagcg
4501 gtcgggctga acggggggtt cgtgcacaca gcccagcttg gagcgaacga cctacaccga
4561 actgagatac ctacagcgtg agctatgaga aagcgccacg cttcccgaag ggagaaaggc
4621 ggacaggtat ccggtaagcg gcagggtcgg aacaggagag cgcacgaggg agcttccagg
4681 gggaaacgcc tggtatcttt atagtcctgt cgggtttcgc cacctctgac ttgagcgtcg
4741 atttttgtga tgctcgtcag gggggcggag cctatggaaa aacgccagca acgcggcctt
4801 tttacggttc ctggcctttt gctggccttt tgctcacatg ttctttcctg cgttatcccc
4861 tgattctgtg gataaccgta ttaccgccat gcat C. pDNR-Dual-Luc 1 gcggccgcat aacttcgtat agcatacatt atacgaagtt atcagtcgac accatggaag (SEQ ID NO:03)
61 acgccaaaaa cataaagaaa ggcccggcgc cattctatcc tctagaggat ggaaccgctg
121 gagagcaact gcataaggct atgaagagat acgccctggt tcctggaaca attgctttta
181 cagatgcaca tatcgaggtg aacatcacgt acgcggaata cttcgaaatg tccgttcggt
241 tggcagaagc tatgaaacga tatgggctga atacaaatca cagaatcgtc gtatgcagtg
301 aaaactctct tcaattcttt atgccggtgt tgggcgcgtt atttatcgga gttgcagttg
361 cgcccgcgaa cgacatttat aatgaacgtg aattgctcaa cagtatgaac atttcgcagc
421 ctaccgtagt gtttgtttcc aaaaaggggt tgcaaaaaat tttgaacgtg caaaaaaaat
481 taccaataat tcagaaaatt attatcatgg attctaaaac ggattaccag ggatttcagt
541 cgatgtacac gttcgtcaca tctcatctac ctcccggttt taatgagtac gattttgtac
601 cagagtcctt tgatcgtgac aaaacaattg cactgataat gaattcctct ggatctactg
661 ggttacctaa gggtgtggcc cttccgcata gaactgcctg cgtcagattc tcgcatgcca
721 gagatcctat ttttggcaat caaatcattc cggatactgc gattttaagt gttgttccat
781 tccatcacgg ttttggaatg tttactacac tcggatattt gatatgtgga tttcgagtcg
841 tcttaatgta tagatttgaa gaagagctgt ttttacgatc ccttcaggat tacaaaattc
901 aaagtgcgtt gctagtacca accctatttt cattcttcgc caaaagcact ctgattgaca
961 aatacgattt atctaattta cacgaaattg cttctggggg cgcacctctt tcgaaagaag
1021 tcggggaagc ggttgcaaaa cgcttccatc ttccagggat acgacaagga tatgggctca
1081 ctgagactac atcagctatt ctgattacac ccgaggggga tgataaaccg ggcgcggtcg
1141 gtaaagttgt tccatttttt gaagcgaagg ttgtggatct ggataccggg aaaacgctgg
1201 gcgttaatca gagaggcgaa ttatgtgtca gaggacctat gattatgtcc ggttatgtaa
1261 acaatccgga agcgaccaac gccttgattg acaaggatgg atggctacat tctggagaca
1321 tagcttactg ggacgaagac gaacacttct tcatagttga ccgcttgaag tctttaatta
1381 aatacaaagg atatcaggtg gcccccgctg aattggaatc gatattgtta caacacccca
1441 acatcttcga cgcgggcgtg gcaggtcttc ccgacgatga cgccggtgaa cttcccgccg
1501 ccgttgttgt tttggagcac ggaaagacga tgacggaaaa agagatcgtg gattacgtcg
1561 ccagtcaagt aacaaccgcg aaaaagttgc gcggaggagt tgtgtttgtg gacgaagtac
1621 cgaaaggtct taccggaaaa ctcgacgcaa gaaaaatcag agagatcctc ataaaggcca
1681 agaagggcgg aaagtccaaa ttgaggatcc gggcccaggt gagtggtcat aatcataatc
1741 ataatcataa tcataatcac aactagccta ggagatcctg gtcatgacta gtgcttggat
1801 tctcaccaat aaaaaacgcc cggcggcaac cgagcgttct gaacaaatcc agatggagtt
1861 ctgaggtcat tactggatct atcaacagga gtccaagcga gctcgatatc aaattacgcc
1921 ccgccctgcc actcatcgca gtactgttgt aattcattaa gcattctgcc gacatggaag
1981 ccatcacaaa cggcatgatg aacctgaatc gccagcggca tcagcacctt gtcgccttgc
2041 gtataatatt tgcccatggt gaaaacgggg gcgaagaagt tgtccatatt ggccacgttt
2101 aaatcaaaac tggtgaaact cacccaggga ttggctgaga cgaaaaacat attctcaata
2161 aaccctttag ggaaataggc caggttttca ccgtaacacg ccacatcttg cgaatatatg
2221 tgtagaaact gccggaaatc gtcgtggtat tcactccaga gcgatgaaaa cgtttcagtt
2281 tgctcatgga aaacggtgta acaagggtga acactatccc atatcaccag ctcaccgtct
2341 ttcattgcca tacgaaattc cggatgagca ttcatcaggc gggcaagaat gtgaataaag
2401 gccggataaa acttgtgctt atttttcttt acggtcttta aaaaggccgt aatatccagc
2461 tgaacggtct ggttataggt acattgagca actgactgaa atgcctcaaa atgttcttta
2521 cgatgccatt gggatatatc aacggtggta tatccagtga ttttttttctc cattttagct
2581 tccttagctc ctgaaagatc cataacttcg tatagcatac attatacgaa gttatgcggc
2641 cgcgacgtcc acatatacct gccgttcact attatttagt gaaatgagat attatgatat -continued

```
2701 tttctgaatt gtgattaaaa aggcaacttt atgcccatgc aacagaaact ataaaaaata
2761 cagagaatga aaagaaacag atagattttt tagttcttta ggcccgtagt ctgcaaatcc
2821 ttttatgatt ttctatcaaa caaaagagga aaatagacca gttgcaatcc aaacgagagt
2881 ctaatagaat gaggtcgaaa agtaaatcgc gcgggtttgt tactgataaa gcaggcaaga
2941 cctaaaatgt gtaaagggca aagtgtatac tttggcgtca ccccttacat attttaggtc
3001 tttttttatt gtgcgtaact aacttgccat cttcaaacag gagggctgga agaagcagac
3061 cgctaacaca gtacataaaa aaggagacat gaacgatgaa catcaaaaag tttgcaaaac
3121 aagcaacagt attaaccttt actaccgcac tgctggcagg aggcgcaact caagcgtttg
3181 cgaaagaaac gaaccaaaag ccatataagg aaacatacgg catttcccat attacacgcc
3241 atgatatgct gcaaatccct gaacagcaaa aaaatgaaaa atatcaagtt cctgagttcg
3301 attcgtccac aattaaaaat atctcttctg caaaaggcct ggacgtttgg gacagctggc
3361 cattacaaaa cgctgacggc actgtcgcaa actatcacgg ctaccacatc gtctttgcat
3421 tagccggaga tcctaaaaat gcggatgaca catcgattta catgttctat caaaaagtcg
3481 gcgaaacttc tattgacagc tggaaaaacg ctggccgcgt ctttaaagac agcgacaaat
3541 tcgatgcaaa tgattctatc ctaaaagacc aaacacaaga atggtcaggt tcagccacat
3601 ttacatctga cggaaaaatc cgtttattct acactgattt ctccggtaaa cattacggca
3661 aacaaacact gacaactgca caagttaacg tatcagcatc agacagctct ttgaacatca
3721 acggtgtaga ggattataaa tcaatctttg acggtgacgg aaaaacgtat caaaatgtac
3781 agcagttcat cgatgaaggc aactacagct caggcgacaa ccatacgctg agagatcctc
3841 actacgtaga agataaaggc cacaaatact tagtatttga agcaaacact ggaactgaag
3901 atggctacca aggcgaagaa tctttattta acaaagcata ctatggcaaa agcacatcat
3961 tcttccgtca agaaagtcaa aaacttctgc aaagcgataa aaaacgcacg gctgagttag
4021 caaacggcgc tctcggtatg attgagctaa acgatgatta cacactgaaa aaagtgatga
4081 aaccgctgat tgcatctaac acagtaacag atgaaattga acgcgcgaac gtctttaaaa
4141 tgaacggcaa atggtacctg ttcactgact cccgcggatc aaaaatgacg attgacggca
4201 ttacgtctaa cgatatttac atgcttggtt atgtttctaa ttctttaact ggcccataca
4261 agccgctgaa caaaactggc cttgtgttaa aaatggatct tgatcctaac gatgtaacct
4321 ttacttactc acacttcgct gtacctcaag cgaaaggaaa caatgtcgtg attacaagct
4381 atatgacaaa cagaggattc tacgcagaca aacaatcaac gtttgcgcct agcttcctgc
4441 tgaacatcaa aggcaagaaa acatctgttg tcaaagacag catccttgaa caaggacaat
4501 taacagttaa caaataaaaa cgcaaaagaa aatgccgata tcctattggc attgacgtca
4561 ggtggcactt ttcggggaaa tgtgcgcgga acccctattt gtttattttt ctaaatacat
4621 tcaaatatgt atccgctcat gagacaataa ccctgataaa tgcttcaata atattgaaaa
4681 aggaagagta tgagtattca acatttccgt gtcgccctta ttcccttttt tgcggcattt
4741 tgccttcctg tttttgctca cccagaaacg ctggtgaaag taaaagatgc tgaagatcag
4801 ttgggtgcac gagtgggtta catcgaactg gatctcaaca gcggtaagat ccttgagagt
4861 tttcgccccg aagaacgttt tccaatgatg agcactttta aagttctgct atgtggcgcg
4921 gtattatccc gtattgacgc cgggcaagag caactcggtc gccgcataca ctattctcag
4981 aatgacttgg ttgagtactc accagtcaca gaaaagcatc ttacggatgg catgacagta
5041 agagaattat gcagtgctgc cataaccatg agtgataaca ctgcggccaa cttacttctg
5101 acaacgatcg gaggaccgaa ggagctaacc gcttttttgc acaacatggg ggatcatgta
5161 actcgccttg atcgttggga accggagctg aatgaagcca taccaaacga cgagcgtgac
5221 accacgatgc ctgtagcaat ggcaacaacg ttgcgcaaac tattaactgg cgaactactt
5281 actctagctt cccggcaaca attaatagac tggatggagg cggataaagt tgcaggacca
5341 cttctgcgct cggcccttcc ggctggctgg tttattgctg ataaatctgg agccggtgag
5401 cgtgggtctc gcggtatcat tgcagcactg gggccagatg gtaagccctc ccgtatcgta
5461 gttatctaca cgacggggag tcaggcaact atggatgaac gaaatagaca gatcgctgag
5521 ataggtgcct cactgattaa gcattggtaa ctgtcagacc aagtttactc atatatactt
5581 tagattgatt taaaacttca tttttaattt aaaaggatct aggtgaagat cctttttgat
5641 aatctcatga ccaaaatccc ttaacgtgag ttttcgttcc actgagcgtc agaccccgta
5701 gaaaagatca aaggatcttc ttgagatcct ttttttctgc gcgtaatctg ctgcttgcaa
5761 acaaaaaaac caccgctacc agcggtggtt tgtttgccgg atcaagagct accaactctt
5821 tttccgaagg taactggctt cagcagagcg cagataccaa atactgttct tctagtgtag
5881 ccgtagttag gccaccactt caagaactct gtagcaccgc ctacatacct cgctctgcta
5941 atcctgttac cagtggctgc tgccagtggc gataagtcgt gtcttaccgg gttggactca
6001 agacgatagt taccggataa ggcgcagcgg tcgggctgaa cggggggttc gtgcacacag
6061 cccagcttgg agcgaacgac ctacaccgaa ctgagatacc tacagcgtga gctatgagaa
6121 agcgccacgc ttcccgaagg gagaaaggcg gacaggtatc cggtaagcgg cagggtcgga
6181 acaggagagc gcacgaggga gcttccaggg ggaaacgcct ggtatcttta tagtcctgtc
6241 gggtttcgcc acctctgact tgagcgtcga tttttgtgat gctcgtcagg ggggcggagc
6301 ctatggaaaa acgccagcaa cgcggccttt ttacggttcc tggccttttg ctggcctttt
6361 gctcacatgt tctttcctgc gttatcccct gattctgtgg ataaccgtat taccgcctta
6421 cgcgtgtaaa acgacggcca gtagatctgt aatacgactc actatagggc gctagctgct
6481 cgccgcagcc gaacgaccga gcgcagcgag tcagtgagcg aggaa
```

D. pLPS-Luc-EGFP

```
  1 tagttattaa tagtaatcaa ttacggggtc attagttcat agaccatata tggagttccg  (SEQ ID NO:04)
 61 cgttacataa cttacggtaa atggcccgcc tggctgaccg cccaacgacc cccgcccatt
121 gacgtcaata atgacgtatg ttcccatagt aacgccaata gggactttcc attgacgtca
181 atgggtggag tatttacggt aaactgccca cttggcagta catcaagtgt atcatatgcc
241 aagtacgccc cctattgacg tcaatgacgg taaatggccc gcctggcatt atgcccagta
301 catgacctta tgggactttc ctacttggca gtacatctac gtattagtca tcgctattac
361 catggtgatg cggttttggc agtacatcaa tgggcgtgga tagcggtttg actcacgggg
421 atttccaagt ctccacccca ttgacgtcaa tgggagtttg ttttggcacc aaaatcaacg
481 ggactttcca aaatgtcgta acaactccgc cccattgacg caaatgggcg gtaggcgtgt
541 acggtgggag gtctatataa gcagagctgg tttagtgaac cgtcagatcc gctagcataa
601 cttcgtatag catacattat acgaagttat cagtcgacac catggaagac gccaaaaaca
661 taaagaaagg cccggcgcca ttctatcctc tagaggatgg aaccgctgga gagcaactgc
721 ataaggctat gaagagatac gccctggttc ctggaacaat tgcttttaca gatgcacata
781 tcgaggtgaa catcacgtac gcggaatact tcgaaatgtc cgttcggttg gcagaagcta
```

-continued 841 tgaaacgata tgggctgaat acaaatcaca gaatcgtcgt atgcagtgaa aactctcttc
901 aattctttat gccggtgttg ggcgcgttat ttatcggagt tgcagttgcg cccgcgaacg
961 acatttataa tgaacgtgaa ttgctcaaca gtatgaacat ttcgcagcct accgtagtgt
1021 ttgtttccaa aaaggggttg caaaaaattt tgaacgtgca aaaaaaatta ccaataattc
1081 agaaaattat tatcatggat tctaaaacgg attaccaggg atttcagtcg atgtacacgt
1141 tcgtcacatc tcatctacct cccggtttta atgagtacga ttttgtacca gagtcctttg
1201 atcgtgacaa aacaattgca ctgataatga attcctctgg atctactggg ttacctaagg
1261 gtgtggccct tccgcataga actgcctgcg tcagattctc gcatgccaga gatcctattt
1321 ttggcaatca aatcattccg gatactgcga ttttaagtgt tgttccattc catcacggtt
1381 ttggaatgtt tactacactc ggatatttga tatgtggatt tcgagtcgtc ttaatgtata
1441 gatttgaaga agagctgttt ttacgatccc ttcaggatta caaaattcaa agtgcgttgc
1501 tagtaccaac cctattttca ttcttcgcca aaagcactct gattgacaaa tacgatttat
1561 ctaatttaca cgaaattgct tctgggggcg cacctctttc gaaagaagtc ggggaagcgg
1621 ttgcaaaacg cttccatctt ccagggatac gacaaggata tgggctcact gagactacat
1681 cagctattct gattacaccc gagggggatg ataaaccggg cgcggtcggt aaagttgttc
1741 cattttttga agcgaaggtt gtggatctgg ataccgggaa aacgctgggc gttaatcaga
1801 gaggcgaatt atgtgtcaga ggacctatga ttatgtccgg ttatgtaaac aatccggaag
1861 cgaccaacgc cttgattgac aaggatggat ggctacattc tggagacata gcttactggg
1921 acgaagacga acacttcttc atagttgacc gcttgaagtc tttaattaaa tacaaaggat
1981 atcaggtggc ccccgctgaa ttggaatcga tattgttaca acaccccaac atcttcgacg
2041 cgggcgtggc aggtcttccc gacgatgacg ccggtgaact tcccgccgcc gttgttgttt
2101 tggagcacgg aaagacgatg acggaaaaag agatcgtgga ttacgtcgcc agtcaagtaa
2161 caaccgcgaa aaagttgcgc ggaggagttg tgtttgtgga cgaagtaccg aaaggtctta
2221 ccggaaaact cgacgcaaga aaaatcagag agatcctcat aaaggccaag aagggcggaa
2281 agtccaaatt gaggatccgg gcccaggtga gtggtcataa tcataatcat aatcataatc
2341 ataatcacaa ctagcctagg agatcctggt catgactagt gcttggattc tcaccaataa
2401 aaaacgcccg gcggcaaccg agcgttctga acaaatccag atggagttct gaggtcatta
2461 ctggatctat caacaggagt ccaagcgagc tcgatatcaa attacgcccc gccctgccac
2521 tcatcgcagt actgttgtaa ttcattaagc attctgccga catggaagcc atcacaaacg
2581 gcatgatgaa cctgaatcgc cagcggcatc agcaccttgt cgccttgcgt ataatatttg
2641 cccatggtga aaacgggggc gaagaagttg tccatattgg ccacgtttaa atcaaaactg
2701 gtgaaactca cccagggatt ggctgagacg aaaaacatat tctcaataaa ccctttaggg
2761 aaataggcca ggttttcacc gtaacacgcc acatcttgcg aatatatgtg tagaaactgc
2821 cggaaatcgt cgtggtattc actccagagc gatgaaaacg tttcagtttg ctcatggaaa
2881 acggtgtaac aagggtgaac actatcccat atcaccagct caccgtcttt cattgccata
2941 cgaaattccg gatgagcatt catcaggcgg gcaagaatgt gaataaaggc cggataaaac
3001 ttgtgcttat ttttctttac ggtctttaaa aaggccgtaa tatccagctg aacggtctgg
3061 ttataggtac attgagcaac tgactgaaat gcctcaaaat gttctttacg atgccattgg
3121 gatatatcaa cggtggtata tccagtgatt tttttctcca ttttagcttc cttagctcct
3181 gaaagatcca taacttcgta tagcatacat tatacgaagt tatagatcca atattattga
3241 agcatttatc agggttattg tctcatgagc ggatacatat ttgaatgtat ttagaaaaat
3301 aaacaaatag gggttccgcg cacatttccc cgaaaagtgc cacctgacgt ggatctcgag
3361 ctcaagcttc gaattcaggg tttccttgac aatatcatac ttatcctgtc cctttttttt
3421 ccacagctac cggtcgcgag caagggcgag gagctgttca ccggggtggt gcccatcctg
3481 gtcgagctgg acggcgacgt aaacggccac aagttcagcg tgtccggcga gggcgagggc
3541 gatgccacct acggcaagct gaccctgaag ttcatctgca ccaccggcaa gctgcccgtg
3601 ccctggccca ccctcgtgac caccctgacc tacggcgtgc agtgcttcag ccgctacccc
3661 gaccacatga agcagcacga cttcttcaag tccgccatgc ccgaaggcta cgtccaggag
3721 cgcaccatct tcttcaagga cgacggcaac tacaagaccc gcgccgaggt gaagttcgag
3781 ggcgacaccc tggtgaaccg catcgagctg aagggcatcg acttcaagga ggacggcaac
3841 atcctggggc acaagctgga gtacaactac aacagccaca acgtctatat catggccgac
3901 aagcagaaga acggcatcaa ggtgaacttc aagatccgcc acaacatcga ggacggcagc
3961 gtgcagctcg ccgaccacta ccagcagaac acccccatcg gcgacggccc cgtgctgctg
4021 cccgacaacc actacctgag cacccagtcc gccctgagca aagaccccaa cgagaagcgc
4081 gatcacatgg tcctgctgga gttcgtgacc gccgccggga tcactctcgg catggacgag
4141 ctgtacaagt aaagcggccg cgactctaga tcataatcag ccataccaca tttgtagagg
4201 ttttacttgc tttaaaaaac ctcccacacc tccccctgaa cctgaaacat aaaatgaatg
4261 caattgttgt tgttaacttg tttattgcag cttataatgg ttacaaataa agcaatagca
4321 tcacaaattt cacaaataaa gcattttttt cactgcattc tagttgtggt ttgtccaaac
4381 tcatcaatgt atcttaaggc gtaaattgta agcgttaata ttttgttaaa attcgcgtta
4441 aatttttgtt aaatcagctc atttttaac caataggccg aaatcggcaa aatcccttat
4501 aaatcaaaag aatagaccga gatagggttg agtgttgttc cagtttggaa caagagtcca
4561 ctattaaaga acgtggactc caacgtcaaa gggcgaaaaa ccgtctatca gggcgatggc
4621 ccactacgtg aaccatcacc ctaatcaagt tttttggggt cgaggtgccg taaagcacta
4681 aatcggaacc ctaaagggag cccccgattt agagcttgac ggggaaagcc ggcgaacgtg
4741 gcgagaaagg aagggaagaa agcgaaagga gcgggcgcta gggcgctggc aagtgtagcg
4801 gtcacgctgc gcgtaaccac cacacccgcc gcgcttaatg cgccgctaca gggcgcgtca
4861 ggtggcactt ttcggggaaa tgtgcgcgga acccctattt gtttattttt ctaaatacat
4921 tcaaatatgt atccgctcat gagacaataa ccctgataaa tgcttcaata atattgaaaa
4981 aggaagagtc ctgaggcgga aagaaccagc tgtggaatgt gtgtcagtta gggtgtggaa
5041 agtccccagg ctccccagca ggcagaagta tgcaaagcat gcatctcaat tagtcagcaa
5101 ccaggtgtgg aaagtcccca ggctccccag caggcagaag tatgcaaagc atgcatctca
5161 attagtcagc aaccatagtc ccgcccctaa ctccgcccat cccgccccta actccgccca
5221 gttccgccca ttctccgcec catggctgac taattttttt tatttatgca gaggccgagg
5281 ccgcctcggc ctctgagcta ttccagaagt agtgaggagg cttttttgga ggcctaggct
5341 tttgcaaaga tcgatcaaga gacaggatga ggatcgtttc gcatgattga acaagatgga
5401 ttgcacgcag gttctccggc cgcttgggtg gagaggctat tcggctatga ctgggcacaa
5461 cagacaatcg gctgctctga tgccgccgtg ttccggctgt cagcgcaggg gcgcccggtt
5521 ctttttgtca agaccgacct gtccggtgcc ctgaatgaac tgcaagacga ggcagcgcgg
5581 ctatcgtggc tggccacgac gggcgttcct tgcgcagctg tgctcgacgt tgtcactgaa -continued

```
5641 gcgggaaggg actggctgct attgggcgaa gtgccggggc aggatctcct gtcatctcac
5701 cttgctcctg ccgagaaagt atccatcatg gctgatgcaa tgcggcggct gcatacgctt
5761 gatccggcta cctgcccatt cgaccaccaa gcgaaacatc gcatcgagcg agcacgtact
5821 cggatggaag ccggtcttgt cgatcaggat gatctggacg aagagcatca ggggctcgcg
5881 ccagccgaac tgttcgccag gctcaaggcg agcatgcccg acggcgagga tctcgtcgtg
5941 acccatggcg atgcctgctt gccgaatatc atggtggaaa atggccgctt ttctggattc
6001 atcgactgtg gccggctggg tgtggcggac cgctatcagg acatagcgtt ggctacccgt
6061 gatattgctg aagagcttgg cggcgaatgg gctgaccgct tcctcgtgct ttacggtatc
6121 gccgctcccg attcgcagcg catcgccttc tatcgccttc ttgacgagtt cttctgagcg
6181 ggactctggg gttcgaaatg accgaccaag cgacgcccaa cctgccatca cgagatttcg
6241 attccaccgc cgccttctat gaaaggttgg gcttcggaat cgttttccgg gacgccggct
6301 ggatgatcct ccagcgcggg gatctcatgc tggagttctt cgcccaccct agggggaggc
6361 taactgaaac acggaaggag acaataccgg aaggaacccg cgctatgacg gcaataaaaa
6421 gaaagaataa aacgcacggt gttgggtcgt ttgttcataa acgcggggtt cggtcccagg
6481 gctggcactc tgtcgatacc ccaccgagac cccattgggg ccaatacgcc cgcgtttctt
6541 ccttttcccc accccacccc ccaagttcgg gtgaaggccc agggctcgca gccaacgtcg
6601 gggcggcagg ccctgccata gcctcaggtt actcatatat actttagatt gatttaaaac
6661 ttcattttta atttaaaagg atctaggtga agatcctttt tgataatctc atgaccaaaa
6721 tcccttaacg tgagttttcg ttccactgag cgtcagaccc cgtagaaaag atcaaaggat
6781 cttcttgaga tccttttttt ctgcgcgtaa tctgctgctt gcaaacaaaa aaaccaccgc
6841 taccagcggt ggtttgtttg ccggatcaag agctaccaac tctttttccg aaggtaactg
6901 gcttcagcag agcgcagata ccaaatactg tccttctagt gtagccgtag ttaggccacc
6961 acttcaagaa ctctgtagca ccgcctacat acctcgctct gctaatcctg ttaccagtgg
7021 ctgctgccag tggcgataag tcgtgtctta ccgggttgga ctcaagacga tagttaccgg
7081 ataaggcgca gcggtcgggc tgaacggggg gttcgtgcac acagcccagc ttggagcgaa
7141 cgacctacac cgaactgaga tacctacagc gtgagctatg agaaagcgcc acgcttcccg
7201 aagggagaaa ggcggacagg tatccggtaa gcggcagggt cggaacagga gagcgcacga
7261 gggagcttcc agggggaaac gcctggtatc tttatagtcc tgtcgggttt cgccacctct
7321 gacttgagcg tcgatttttg tgatgctcgt caggggggcg gagcctatgg aaaaacgcca
7381 gcaacgcggc ctttttacgg ttcctggcct tttgctggcc ttttgctcac atgttctttc
7441 ctgcgttatc ccctgattct gtggataacc gtattaccgc catgcat
```

EXAMPLE 3

Representative Splice Donor and Acceptor Sites

A. Consensus Splice Donor and Acceptor Oligos:

Consensus Splice Donor:

(cloned into pDNR-1 at ApaI and AvrII sites)

```
Site of Exon/intron boundary      _|__
top:                              CAGGTGAGTTAGGTAAGTGAACATGGTCATAGCTGTTTC       (SEQ ID NOS:05 & 06)

bottom:                       CCGGGTCCACTCAATCCATTCACTTGTACCAGTATCGACAAAGGATC
```

Consensus Splice Acceptor (Includes Branch Site):

(cloned into pEGFP-N1 at EcoRI and AgeI sites)

```
Site of Exon/intron boundary                                      _|__
top    : AATTCAGGGTTTCCTTGACAATATCATACTTATCCTGTCCCTTTTTTTTCCACAGCTA      (SEQ ID NOS:07 & 08)

bottom:     GTCCCAAAGGAACTGTTATAGTATGAATAGGACAGGGAAAAAAAAGGTGTCGATGGCC
```

B. Splice Donor from Human Hemoglobin Beta Sequence Encoding Exon and Intron Sequence Flanking the Start of Human Hemoglobin Beta Intron I:

```
Site of Exon/intron boundary                  _|__
top    :              AGTTGGTGGTGAGGCCCTGGGCAGGTTGGTATCAAGGTTACAAGACAGGT   (SEQ ID NOS:09 & 10)

bottom:               TCAACCACCACTCCGGGACCCGTCCAACCATAGTTCCAATGTTCTGTCCA
```

This splice donor sequence was encoded within the following oligo to enable cloning into pDNR-1 at the ApaI and AvrII sites. Note that this oligo was additionally designed to place stop codons (TAG and TM) in the two unused reading frames present in the MCS of pDNR-1. (The frame utilized is defined as starting with the first base of the loxP site in pDNR-1). In addition, remaining in frame with the utilized frame is encoded an (HN)6 tag to enable protein purification in bacteria—this is encoded directly after the intron seq shown above.

Oligo for Splice Donor from Human Hemoglobin Intron I with Added Stops and (HN)6 tag:

```
Site of Exon/intron boundary
Top:
CGTAGTGTAAAGTTGGTGGTGAGGCCCTGGGCAGGTTGGTATCAAGGTTACAAGACAGGTCATAATCATAATCATAATCATA (SEQ ID NOS:11 & 12)
ATCATAATCACAACTAGC

Bottom:
CCGGGCATCACATTTCAACCACCACTCCGGGACCCGTCCAACCATAGTTCCAATGTTCTGTCCAGTATTAGTATTAGTATTA
GTATTAGTATTAGTGTTGATCGGATC
```

Sequence for (HN)6 Tag Within Splice Donor Oligo:

```
Top    :           GGT CAT AAT CAT AAT CAT AAT CAT AAT CAT AAT CAC AAC TAG   (SEQ ID NOS:13, 14, and 15)

Bottom:            CCA GTA TTA GTA TTA GTA TTA GTA TTA GTA TTA GTG TTG ATC

Peptide encoded:   Gly His Asn His Asn His Asn His Asn His Asn His Asn stop
```

Splice Acceptor From Human Hemoglobin Beta

This oligo encodes the splice Acceptor region of intron I from Human Hemoglobin Beta together with flanking exoon sequence. It was cloned into pEGFP-N1 at the AgeI and EcoR I sites.

```
Oligo for Human Hemoglobin Beta splice acceptor from Intron I:
Site of Exon/intron boundary

Top    :
AATTCTTGGGTTTCTGATAGGCACTGACTCTCTCTGCCGATTGGTCTATTTTCCCACCCTTAGGCTGCTGGTGGTCTACC  (SEQ ID NOS:16 & 17)
CTTGGACCCTA

Bottom:
GAACCCAAAGACTATCCGTGACTGAGAGAGACGGCTAACCAGATAAAAGGGTGGGAATCCGACGACCACCAGATGGGAAC
CTGGGATGGCC
```

It is evident from the above results and discussion that the subject invention provides an efficient method to transfer a nucleic acid from a first vector to a second vector, where the subject methods do not employ digestion and ligation protocols. Advantages provided by the subject invention include: the ability to transfer or clone a nucleic acid of interest from a single donor into a variety of different expression vectors at substantially the same time and in a known orientation and reading frame; the ability to readily identify successful clones; the ability to transfer many different genes to one or more expression vectors simultaneously; no longer needing to sequence the junctions of the transferred fragment and the expression vector or to resequence the gene transferred and the like. Another advantage of the subject invention is to provide for introns in the product vector, so as to remove any unwanted sequences from the final encoded product, and/or easily produce N- and/or C-terminal tagged fusion proteins. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A composition for use in preparing an intron containing vector, said composition comprising:

a donor vector comprising at least one splice site and an acceptor vector comprising at least one splice site, wherein said donor and acceptor vectors each comprise at least one sequence-specific recombinase target site and wherein one of said donor and acceptor vectors comprises two sequence-specific recombinase target sites and the other of said donor and acceptor vectors comprises a single sequence-specific recombinase target site, wherein all of said sequence-specific recombinase target sites are able to recombine with each other.

2. The composition according to claim 1, wherein said donor vector comprises two sequence-specific recombinase target sites and said acceptor vector comprises a single sequence-specific recombinase target site.

3. The composition according to claim 2, wherein said two sequence-specific recombinase target sites on said donor vector are oriented in the same direction.

4. The composition according to claim 1, wherein said donor vector comprises a single sequence-specific recombinase target site and said acceptor comprises two sequence-specific recombinase target sites.

5. The composition according to claim 4, wherein said two sequence-specific recombinase target sites of said acceptor vector are oriented in the same direction.

6. The composition according to claim 1, wherein said system further comprises a sequence specific recombinase.

7. The composition according to claim 1, wherein said sequence-specific recombinase target sites are selected from the group consisting of: lox sites, att sites, dif sites and frt sites.

8. The composition according to claim 1, wherein said donor and acceptor vectors are plasmids, cosmids, bacs, yacs or viruses.

9. The composition according to claim 1 wherein said composition has been inserted.

10. The composition according to claim 1, wherein said at least one splice site in each of said donor and acceptor vectors comprises a splice donor and a splice acceptor sequence.

11. A kit for use in a producing an expression vector, said kit comprises:

(a) a donor vector comprising a splice site; and (b) an acceptor vector comprising a splice site;

wherein each of said donor and acceptor vectors further comprises at least one sequence-specific recombinase target site and wherein one of said donor and acceptor vectors comprises two sequence-specific recombinase target sites and the other of said donor and acceptor vectors comprises a single sequence-specific recombinase target site, wherein all of said sequence-specific recombinase target sites are able to recombine with each other.

12. The kit according to claim 11, wherein said kit further comprises a sequence specific recombinase that recognizes said sequence-specific recombinase target sites.

13. A method of producing an intron containing vector, said method comprising:

combining a splice site comprising donor vector and a splice sequence comprising acceptor vector, wherein one of said donor and acceptor vectors comprises two sequence-specific recombinase target sites and the other of said donor and acceptor vectors comprises a single sequence-specific recombinase target site, wherein all of said sequence-specific recombinase target sites are able to recombine with each other, with a recombinase under conditions sufficient for site-specific recombination to occur to produce said intron containing vector.

14. The method according to claim 13, wherein said donor vector comprises two sequence-specific recombinase target sites and said acceptor vector comprises a single sequence-specific recombinase target site.

15. The method according to claim 13, wherein said donor vector comprises a single sequence-specific recombinase target site and said acceptor vector comprises two sequence-specific recombinase target sites.

16. The method according to claim 13, wherein said sequence specific recombinase is selected from the group consisting of: recombinases, transposases and integrases.

17. The method according to claim 13, wherein said sequence specific recombinase is Cre recombinase.

18. The method according to claim 13, wherein said sequence-specific recombinase target sites are selected from the group consisting of: lox sites, att sites, dif sites and frt sites.

19. The method according to claim 18, wherein said recombinase recognition sites are lox sites.

* * * * *

UNITED STATES PATENT AND TRADEMARK OFFICE

CERTIFICATE OF CORRECTION

PATENT NO. : 6,977,165 B2
DATED : December 20, 2005
INVENTOR(S) : Andrew Alan Farmer It is certified that error appears in the above-identified patent and that said Letters Patent is hereby corrected as shown below:

Column 66,
Line 57, replace "has been inserted" with -- further comprises a host cell --.

Signed and Sealed this

Fourth Day of April, 2006

JON W. DUDAS
*Director of the United States Patent and Trademark Office*